United States Patent
Mukai et al.

(10) Patent No.: US 11,357,670 B2
(45) Date of Patent: Jun. 14, 2022

(54) ABSORBENT ARTICLE WITH LEAK-PROOF WALLS

(71) Applicant: UNICHARM CORPORATION, Shikokuchuo (JP)

(72) Inventors: Hirotomo Mukai, Kagawa (JP); Takahito Nagai, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 807 days.

(21) Appl. No.: 16/307,144

(22) PCT Filed: Jun. 5, 2017

(86) PCT No.: PCT/JP2017/020864
§ 371 (c)(1),
(2) Date: Dec. 5, 2018

(87) PCT Pub. No.: WO2017/213096
PCT Pub. Date: Dec. 14, 2017

(65) Prior Publication Data
US 2019/0262194 A1    Aug. 29, 2019

(30) Foreign Application Priority Data
Jun. 6, 2016  (JP) .............................. JP2016-112923

(51) Int. Cl.
*A61F 13/494*    (2006.01)
*A61F 13/49*    (2006.01)
(Continued)

(52) U.S. Cl.
CPC ........ *A61F 13/4942* (2013.01); *A61F 13/475* (2013.01); *A61F 13/494* (2013.01);
(Continued)

(58) Field of Classification Search
CPC .............. A61F 13/475; A61F 13/49014; A61F 13/494; A61F 13/4942; A61F 13/496;
(Continued)

(56) References Cited

U.S. PATENT DOCUMENTS 4,636,207 A * 1/1987 Buell .................. A61F 13/4942
  604/370
4,834,735 A * 5/1989 Alemany .............. A61F 13/511
  604/368
(Continued)

FOREIGN PATENT DOCUMENTS

CN    1426771 A    7/2003
CN    102427788 A    4/2012
(Continued)

OTHER PUBLICATIONS

International Search Report in PCT Application No. PCT/JP2017/020864, dated Aug. 29, 2017, 4pp.
(Continued)

*Primary Examiner* — Michele M Kidwell
(74) *Attorney, Agent, or Firm* — Hauptman Ham, LLP

(57) ABSTRACT

An absorbent article including an absorbent main body including an absorbent core; and a pair of leak-proof walls. The pair of leak-proof walls are on respective widthwise side portions of the absorbent main body. Each of the leak-proof walls is capable of standing on a skin side in the thickness direction. The absorbent core includes a low-basis-weight portion in a widthwise central portion. The low-basis-weight portion has a basis weight of the absorbent core smaller than the basis weight in a surrounding portion. A joined part is formed by joining a surface of the skin-side portion and a surface of the non-skin-side portion, the surfaces facing to each other. The joined part is provided inside a distal end of the leak-proof wall and outside the low-basis-weight portion in the width direction. A part of the
(Continued)

joined part and a part of the low-basis-weight portion overlap in the longitudinal direction.

12 Claims, 11 Drawing Sheets

(51) Int. Cl.
*A61F 13/496* (2006.01)
*A61F 13/532* (2006.01)
*A61F 13/535* (2006.01)
*A61F 13/475* (2006.01)

(52) U.S. Cl.
CPC ...... *A61F 13/496* (2013.01); *A61F 13/49014* (2013.01); *A61F 13/532* (2013.01); *A61F 13/535* (2013.01); *A61F 2013/49025* (2013.01); *A61F 2013/4948* (2013.01)

(58) Field of Classification Search
CPC .......... A61F 13/532; A61F 2013/49025; A61F 2013/49042; A61F 2013/49088
See application file for complete search history.

(56) References Cited

U.S. PATENT DOCUMENTS

| | | | | |
|---|---|---|---|---|
| 5,476,458 | A * | 12/1995 | Glaug | A61F 13/15203 |
| | | | | 604/358 |
| 5,624,426 | A * | 4/1997 | Roe | A61F 13/4942 |
| | | | | 604/385.28 |
| 6,468,257 | B1 * | 10/2002 | Ono | A61F 13/505 |
| | | | | 604/391 |
| 6,641,570 | B2 * | 11/2003 | Mishima | A61F 13/495 |
| | | | | 604/385.28 |
| 6,837,879 | B2 * | 1/2005 | Kuen | A61F 13/4942 |
| | | | | 604/385.28 |
| 7,410,479 | B2 * | 8/2008 | Hoshino | A61F 13/49019 |
| | | | | 604/385.24 |
| 8,361,047 | B2 * | 1/2013 | Mukai | A61F 13/49413 |
| | | | | 604/385.27 |
| 2005/0004545 | A1 * | 1/2005 | Shimada | A61F 13/4946 |
| | | | | 604/385.01 |
| 2005/0131375 | A1 * | 6/2005 | Sasaki | A61F 13/4942 |
| | | | | 604/385.28 |
| 2005/0148988 | A1 | 7/2005 | Kinoshita et al. | |
| 2010/0305532 | A1 * | 12/2010 | Ashton | A61F 13/5323 |
| | | | | 604/365 |
| 2011/0196325 | A1 * | 8/2011 | Isele | A61F 13/4942 |
| | | | | 604/365 |
| 2014/0288521 | A1 | 9/2014 | Wade et al. | |
| 2016/0270978 | A1 * | 9/2016 | Raycheck | A61F 13/49406 |
| 2019/0328586 | A1 * | 10/2019 | Mukai | A61F 13/49413 |

FOREIGN PATENT DOCUMENTS

| | | |
|---|---|---|
| EP | 0613361 A1 | 9/1994 |
| EP | 2082713 A1 | 7/2009 |
| EP | 2246018 A1 | 11/2010 |
| JP | H4-12751 A | 1/1992 |
| JP | 2003-245306 A | 9/2003 |
| JP | 2007-143697 A | 6/2007 |
| JP | 2008142340 A | 6/2008 |
| JP | 2009-61052 A | 3/2009 |
| JP | 2010-131073 A | 6/2010 |
| JP | 2010-264161 A | 11/2010 |
| JP | 2013-374 A | 1/2013 |
| JP | 2013-13524 A | 1/2013 |
| JP | 2013-255571 A | 12/2013 |
| WO | 93/09739 A1 | 5/1993 |
| WO | 2011162069 A1 | 12/2011 |

OTHER PUBLICATIONS

Extended European Search Report in EP Application No. 17810271.1, dated Apr. 8, 2019, 9pp.
Office Action in CN Application No. 201780035052.4, dated Nov. 20, 2020, 11pp.
International Preliminary Report on Patentability in PCT Application No. PCT/JP2017/020864, dated Aug. 29, 2017, 26pp.
Office Action in ID Application No. P00201900064, dated Dec. 22, 2020, 5pp.
Office Action in IN Application No. 201827042461, dated Jun. 16, 2021, 6pp.

* cited by examiner

ABSORBENT ARTICLE WITH LEAK-PROOF WALLS

RELATED APPLICATIONS

The present application is a national phase of International Application Number PCT/JP2017/020864, filed Jun. 5, 2017, which claims priority to Japanese Application Number 2016-112923, filed Jun. 6, 2016.

TECHNICAL FIELD

The present invention relates to an absorbent article.

BACKGROUND ART

A pull-on disposable diaper can be illustrated as an absorbent article. PTL 1 discloses a pull-on disposable diaper which includes a waist covering member and a body-fluid absorbent panel member, and in which side flaps (leak-proof walls) are formed on both widthwise sides of the panel member. In this pull-on disposable diaper, a cord of elastic member is attached to a free edge portion of each of the side flaps in an extended state. The free edge portions of the side flaps are brought into close contact with the groin of a wearer during wearing to prevent side leakage of body fluid.

CITATION LIST

Patent Literature

[PTL 1] Japanese Patent Application Publication No. 2009-61052

SUMMARY OF INVENTION

Technical Problem

However, in the pull-on disposable diaper described in the foregoing PTL 1, the side flaps linearly stand from the side edges of a body-fluid-absorbent core material, coming into close contact with a wearer's groin. This makes the side flaps stand unstable and makes the contact poor. Accordingly, the free edge portions of the side flaps tend to fall apart from the groin due to droop of the core material caused by body fluid absorption or due to the wearer's movement. This makes an effect of side leakage prevention insufficient.

The present invention has been devised in view of the conventional problems described above, and an object of the present invention is to provide an absorbent article with an improved effect of side leakage prevention.

A primary aspect of the disclosure is an absorbent article including:
  an absorbent main body including an absorbent core and having a longitudinal direction, a width direction, and a thickness direction that intersect one another,
    the absorbent core including a low-basis-weight portion in a widthwise central portion,
    the low-basis-weight portion being a portion in which a basis weight of the absorbent core is smaller than the basis weight in a surrounding of the portion;
  a pair of leak-proof walls provided on respective widthwise side portions of the absorbent main body,
    each of the leak-proof walls including an elastic member that stretches and contracts in the longitudinal direction,
    each of the leak-proof walls being capable of standing on a skin side in the thickness direction,
    each of the leak-proof walls including a skin-side portion and a non-skin-side portion,
      the non-skin-side portion disposed on a non-skin side in the thickness direction with respect to the skin-side portion; and
  a joined part provided inside a distal end of the leak-proof wall and outside the low-basis-weight portion in the width direction,
    the joined part formed by joining at least partially a surface of the skin-side portion and a surface of the non-skin-side portion, the surfaces facing to each other,
    a part of the joined part and a part of the low-basis-weight portion at least overlapping in the longitudinal direction.

Other features of the present disclosure will be made clear from the descriptions of the present specification with reference to the accompanying drawings.

Advantageous Effects of Invention

According to the present invention, it is possible to provide an absorbent article with an improved effect of side leakage prevention.

DESCRIPTION OF EMBODIMENTS

Figure 1:
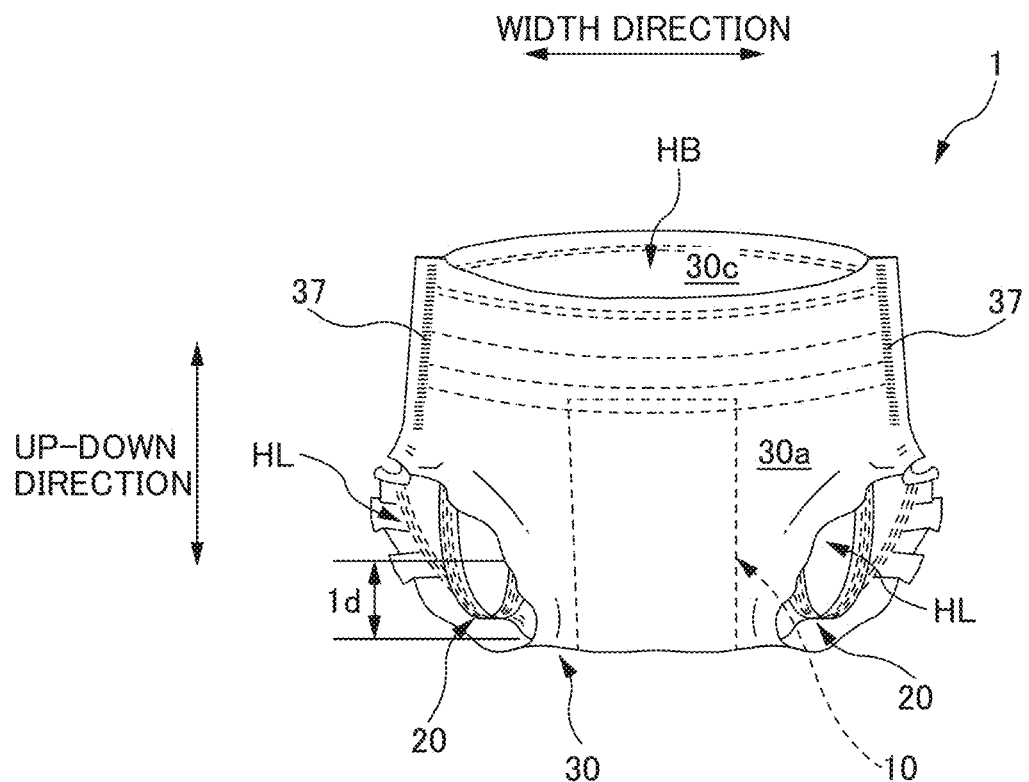
FIG. 1 is a schematic perspective view of a pull-on disposable diaper 1.

An absorbent article including:
  an absorbent main body including an absorbent core and having a longitudinal direction, a width direction, and a thickness direction that intersect one another,
    the absorbent core including a low-basis-weight portion in a widthwise central portion,
    the low-basis-weight portion being a portion in which a basis weight of the absorbent core is smaller than the basis weight in a surrounding of the portion;

a pair of leak-proof walls provided on respective widthwise side portions of the absorbent main body,
    each of the leak-proof walls including an elastic member that stretches and contracts in the longitudinal direction,
    each of the leak-proof walls being capable of standing on a skin side in the thickness direction,
    each of the leak-proof walls including a skin-side portion and a non-skin-side portion,
        the non-skin-side portion disposed on a non-skin side in the thickness direction with respect to the skin-side portion; and
a joined part provided inside a distal end of the leak-proof wall and outside the low-basis-weight portion in the width direction,
    the joined part formed by joining at least partially a surface of the skin-side portion and a surface of the non-skin-side portion, the surfaces facing to each other,
    a part of the joined part and a part of the low-basis-weight portion at least overlapping in the longitudinal direction.

With such an absorbent article, a surface shape of the skin-side portion is maintained by the joined part. The skin-side portion (in particular, the joined part) is in close surface-to-surface contact with the wearer. Since the leak-proof wall is supported by the side portion of the absorbent core standing from the low-basis-weight portion, the joined part easily enters the wearer's groin. A state in which the skin-side portion is in close surface-to-surface contact with the wearer is easily maintained. Accordingly, a gap is hardly formed between the leak-proof wall and the wearer. An effect of side leakage prevention is improved.

In such an absorbent article,
    the joined part is disposed inside an outermost widthwise end in a part of the absorbent core, and
    the part is where the low-basis-weight portion is provided.

With such an absorbent article, it is possible for the leak-proof wall to be stably supported by the side portion of the absorbent core standing from the low-basis-weight portion, maintaining close surface-to-surface contact of the skin-side portion with the wearer.

In such an absorbent article,
    a widthwise length of the low-basis-weight portion is larger than a widthwise length of the joined part.

With such an absorbent article, the side portion of the absorbent core is easily standing from the low-basis-weight portion and easily supports the leak-proof wall. A downward force received by the joined part from the wearer is reduced, preventing the non-skin-side portion from being hindered standing and making it possible for the non-skin-side portion to support the skin-side portion. Consequently, close surface-to-surface contact of the skin-side portion with the wearer is easily maintained.

In such an absorbent article,
    a widthwise length of the non-skin-side portion is larger than a widthwise length of the skin-side portion.

With such an absorbent article, the height of standing of the non-skin-side portion can be secured. A downward force received by the skin-side portion from the wearer is reduced, preventing the non-skin-side portion from being hindered standing and making it possible for the non-skin-side portion to support the skin-side portion. Consequently, close surface-to-surface contact of the skin-side portion with the wearer is easily maintained.

In such an absorbent article,
    the absorbent core includes an upper-layer core and a lower-layer core disposed on the non-skin side in the thickness direction with respect to the upper-layer core,
    the low-basis-weight portion is provided in the lower-layer core,
    the low-basis-weight portion includes a side low-basis-weight portion provided in a widthwise side portion of the absorbent core, and
    a part of the upper-layer core overlapping the side low-basis-weight portion in the longitudinal direction is disposed inside an outer widthwise end of the side low-basis-weight portion.

With such an absorbent article, since the upper-layer core is absent outside the side low-basis-weight portion in the width direction, the side portion of the absorbent core (the lower-layer core) easily stands and easily supports the leak-proof wall. This makes it easier to maintain close surface-to-surface contact of the skin-side portion with the wearer.

In such an absorbent article,
    a longitudinal back end portion of the joined part is located on a back side in the longitudinal direction with respect to the low-basis-weight portion, and
    the longitudinal back end portion is placed on the upper-layer core and the lower-layer core in the thickness direction.

With such an absorbent article, the longitudinal back end portion of the joined part is pushed up by the upper-layer core and the lower-layer core, making it easier to maintain close contact with the wearer.

In such an absorbent article,
    a longitudinal length of the joined part is larger than a longitudinal length of the low-basis-weight portion.

With such an absorbent article, the skin-side portion is in close surface-to-surface contact with the wearer over a wide longitudinal range.

In such an absorbent article,
    a longitudinal center of the low-basis-weight portion and a longitudinal center of the joined part are located on a front side with respect to a longitudinal center of the absorbent article.

With such an absorbent article, in a region of the absorbent article which comes into contact with a wearer's excretion part and in which side leakage easily occurs, the side portion of the absorbent core stands on the low-basis-weight portion, making it possible to support the leak-proof wall and maintaining close surface-to-surface contact of the skin-side portion with the wearer.

In such an absorbent article,
    an inner widthwise side portion of the skin-side portion and the non-skin-side portion includes a plurality of the elastic members,
    an outer widthwise side portion of the skin-side portion includes a plurality of the elastic members, and
    a longitudinal stretching/contracting force per unit width in the width direction of the inner side portion is equal to or larger than a longitudinal stretching/contracting force per unit width in the width direction of the outer side portion.

With such an absorbent article, it is possible to securely bring the joined part into close contact with the wearer by the stretching/contracting force of the inner side portion. And, it is possible to prevent the skin-side portion from returning and falling inwardly caused by the stretching/contracting force of the outer side portion. The skin-side portion is in close surface-to-surface contact with the wearer.

In such an absorbent article,
the absorbent article further comprises an exterior body including
a front waist portion located on one end side of the absorbent main body,
a back waist portion located on another end side of the absorbent main body, and
a crotch portion located between the front waist portion and the back waist portion,
the joined part is at least disposed in a position where a part of the crotch portion overlaps in the longitudinal direction,
the absorbent article is of a pull-on disposable type in which widthwise side portions of the back waist portion are joined to respective widthwise side portions of the front waist portion, and
the absorbent article has an up-down direction and the width direction, and
in an appearance of the absorbent article from the front waist portion side,
at least a part of the leak-proof wall in a lower end region in the up-down direction is exposed from the exterior body in the width direction.

With such an absorbent article, it is possible to prevent the leak-proof wall from being covered by the exterior body. This makes it possible for the skin-side portion of the leak-proof wall to come into close surface-to-surface contact with the wearer while being opened by a wearer's leg at the time of putting on the absorbent article. Also, this makes it possible to prevent side leakage.

An absorbent article including:
an absorbent main body including an absorbent core and having a longitudinal direction, a width direction, and a thickness direction that intersect one another;
a pair of leak-proof walls provided on respective widthwise side portions of the absorbent main body,
each of the leak-proof walls including an elastic member that stretches and contracts in the longitudinal direction,
each of the leak-proof walls being capable of standing on a skin side in the thickness direction,
each of the leak-proof walls including a skin-side portion and a non-skin-side portion,
the non-skin-side portion disposed on a non-skin side in the thickness direction with respect to the skin-side portion; and
a joined part provided inside a distal end of the leak-proof wall in the width direction,
the joined part formed by joining at least partially a surface of the skin-side portion and a surface of the non-skin-side portion, the surfaces facing to each other,
the elastic member is provided at at least either one of a widthwise position inside the joined part and a widthwise position where the elastic member overlaps the joined part.

With such an absorbent article, the joined part can be securely brought into close contact with the wearer by the stretching/contracting force of the elastic member.

An absorbent article including:
an absorbent main body including an absorbent core and having a longitudinal direction, a width direction, and a thickness direction that intersect one another;
a pair of leak-proof walls provided on respective widthwise side portions of the absorbent main body,
each of the leak-proof walls including an elastic member that stretches and contracts in the longitudinal direction,
each of the leak-proof walls being capable of standing on a skin side in the thickness direction,
each of the leak-proof walls including a skin-side portion and a non-skin-side portion,
the non-skin-side portion disposed on a non-skin side in the thickness direction with respect to the skin-side portion; and
a joined part provided inside a distal end of the leak-proof wall in the width direction,
the joined part formed by joining at least partially a surface of the skin-side portion and a surface of the non-skin-side portion, the surfaces facing to each other,
the skin-side portion, the non-skin-side portion, and the joined part are disposed outside the absorbent core in the width direction.

With such an absorbent article, the skin-side portion, the non-skin-side portion, and the joined part can uniformly stand on a position not overlapping the absorbent core.

In such an absorbent article,
the elastic member includes, in the width direction:
an inner elastic member provided in at least either one of and a position inside the joined part and a position where the elastic member overlaps the joined part; and
an outer elastic member provided in a position outside the joined part, and
a minimum widthwise length from an outer side end of the joined part to the outer elastic member is larger than a minimum widthwise length from the outer side end of the joined part to the inner elastic member.

With such an absorbent article, an outer gather section from the outer side end of the joined part to the distal end of the leak-proof wall in the width direction easily maintains a surface shape. The outer gather section can come in close surface-to-surface contact with the wearer.

In such an absorbent article,
With such an absorbent article, the outer gather section easily maintains the surface shape. The outer gather section can come in close surface-to-surface contact with the wearer.

An embodiment is explained below with reference to a "pull-on disposable diaper" for adult as an example of an absorbent article of the present invention.

Embodiment

<Basic Configuration of Pull-on Disposable Diaper 1>

Figure 2:
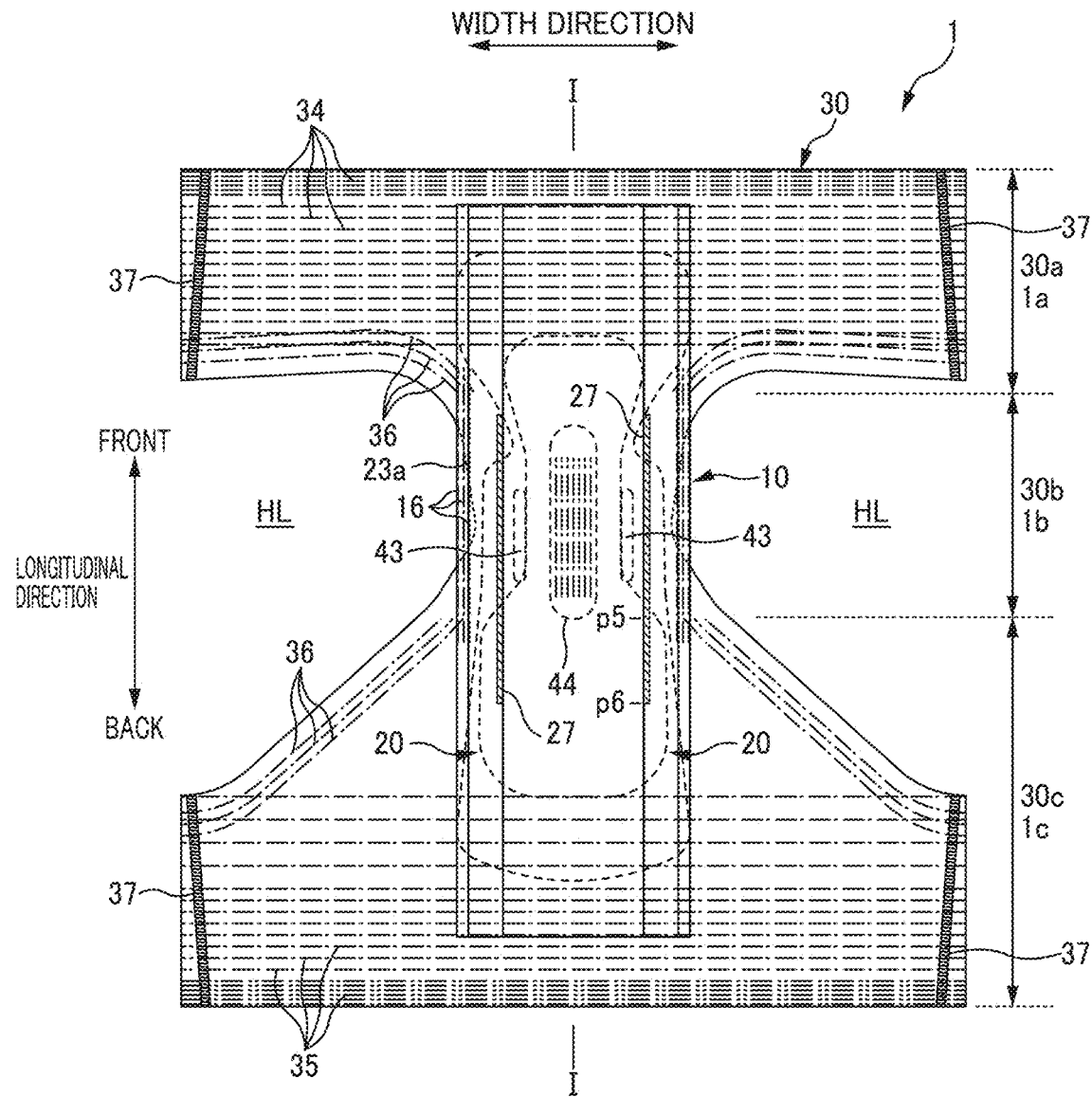
FIG. 2 is a schematic plan view of a diaper in an unfolded and extended state viewed from a skin side of a wearer.
Figure 3:
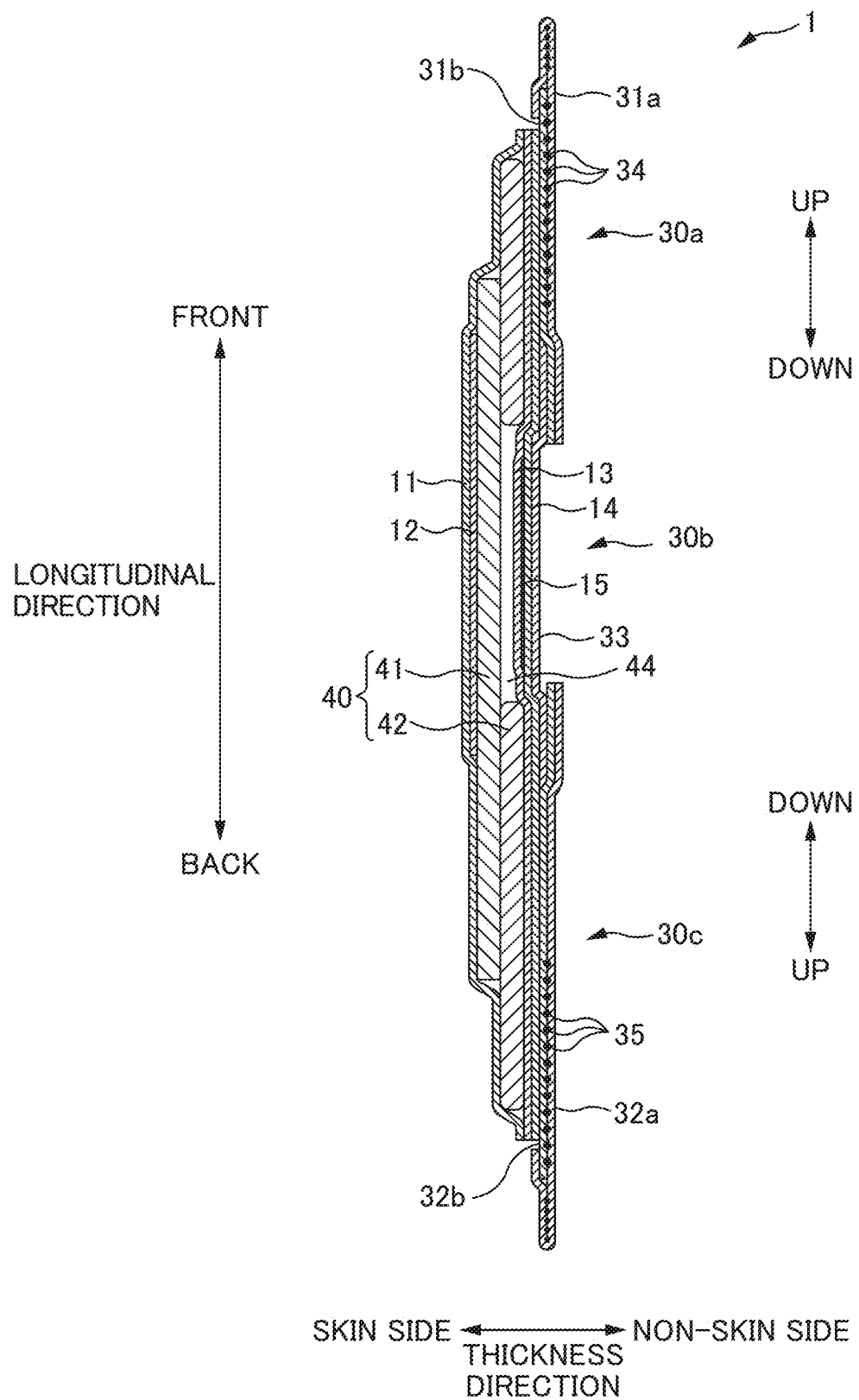
FIG. 3 is a I-I line sectional view of FIG. 2.
Figure 4:
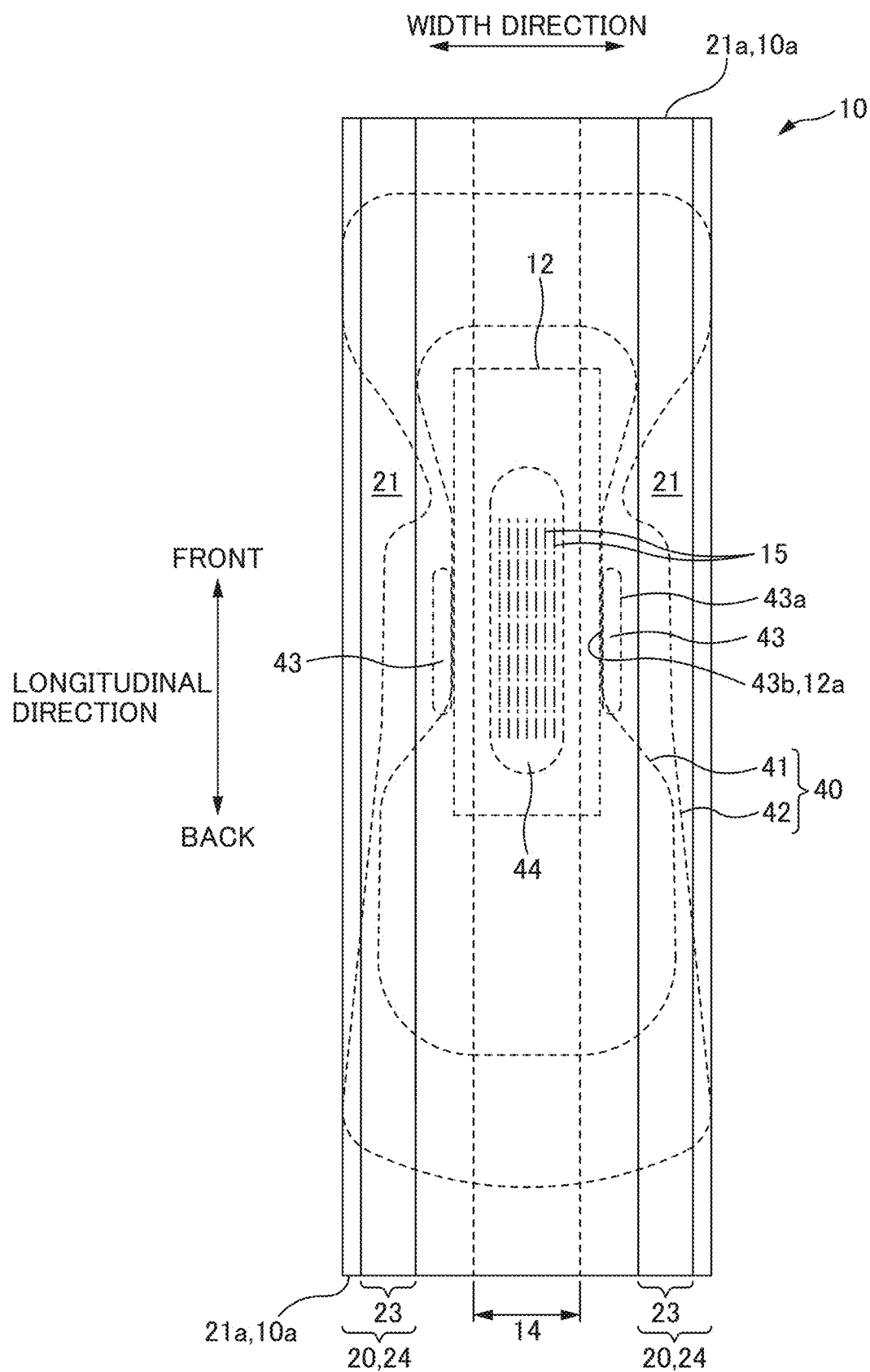
FIG. 4 is a schematic plan view of an absorbent main body in the diaper in the unfolded and extended state viewed from the skin side of the wearer.
Figure 5:
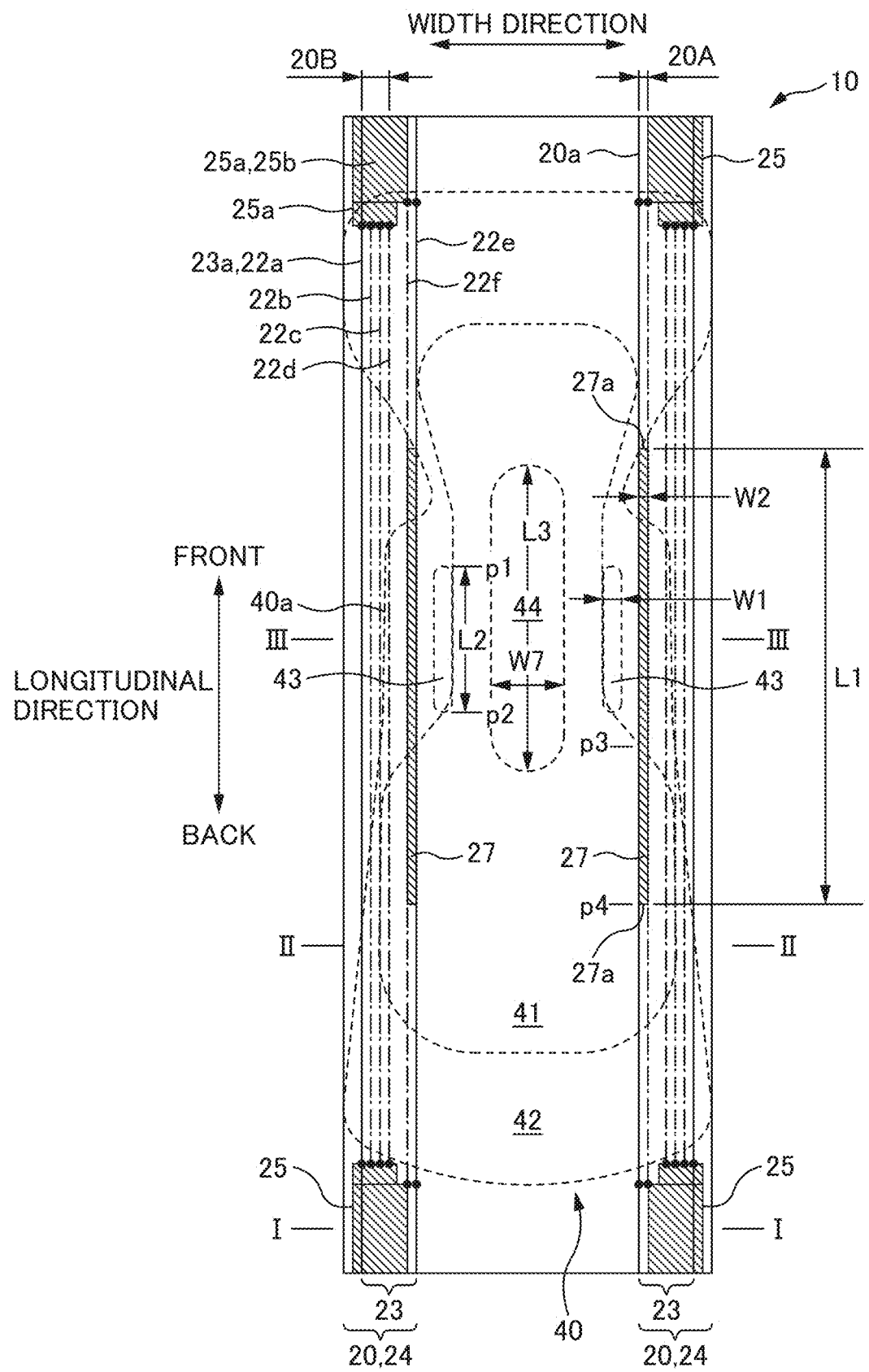
FIG. 5 is a schematic plan view of the absorbent main body in the diaper in the unfolded and extended state viewed from the skin side of the wearer.
Figure 6A:
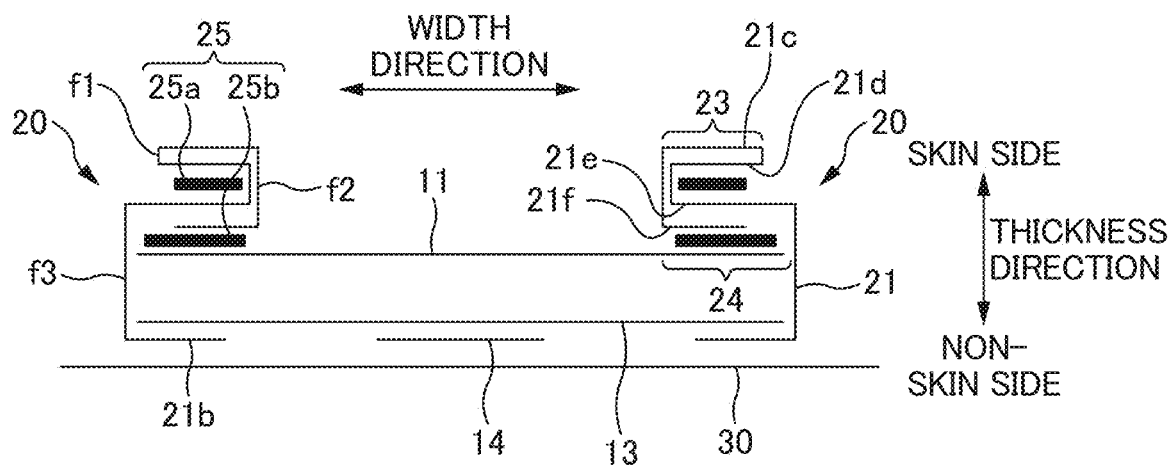
FIG. 6A is a I-I line sectional view of FIG. 5.
Figure 6B:
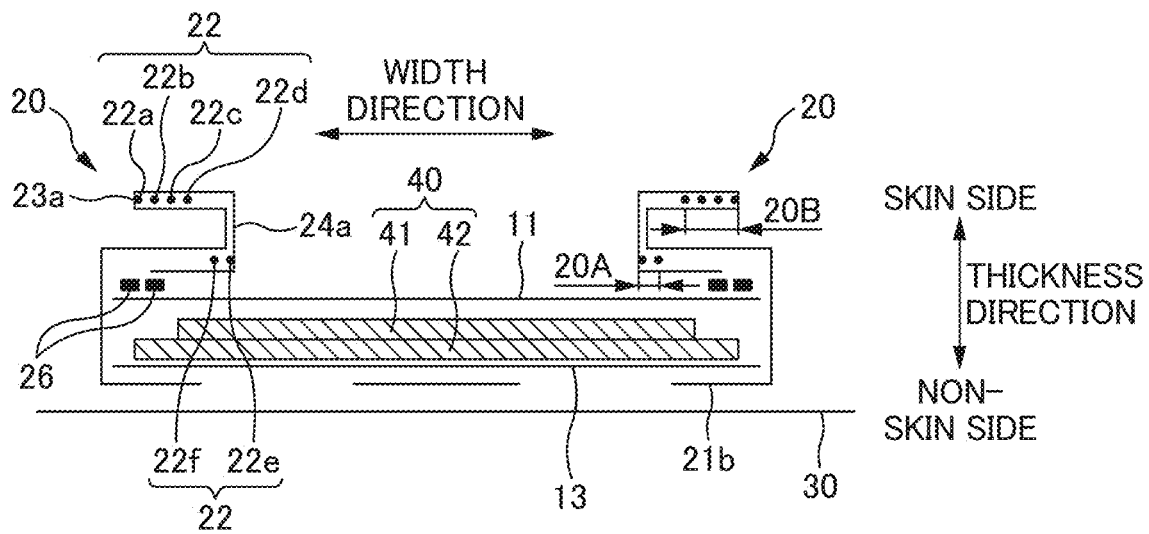
FIG. 6B is a II-II line sectional view of FIG. 5.
Figure 6C:
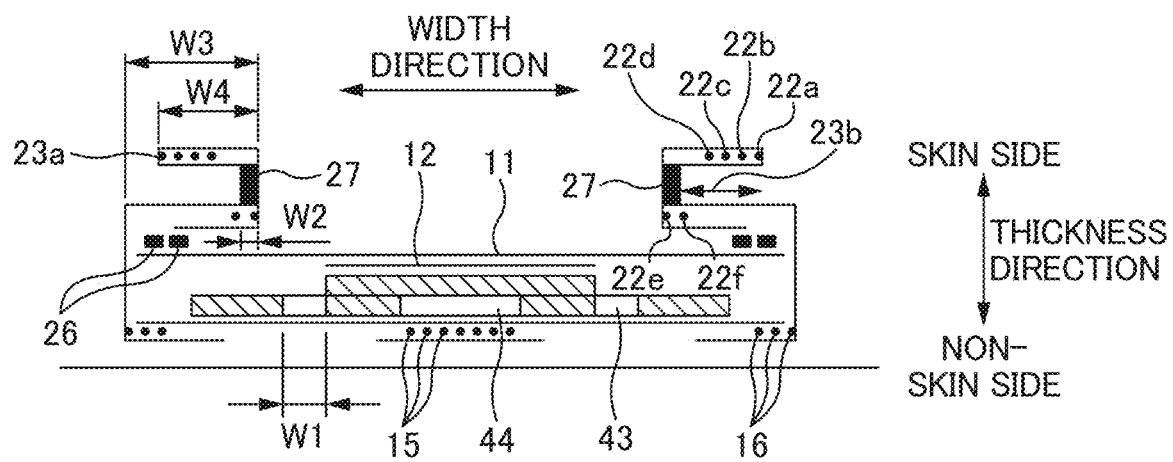
FIG. 6C is a III-III line sectional view of FIG. 5.

FIG. 1 is a schematic perspective view of a pull-on disposable diaper (hereinafter, diaper) 1. FIG. 2 is a schematic plan view of the diaper 1 in an unfolded and extended state viewed from a skin side of a wearer. FIG. 3 is a I-I line sectional view of FIG. 2. FIG. 4 and FIG. 5 are schematic plan views of an absorbent main body 10 in the diaper 1 in the unfolded and extended state viewed from the skin side of the wearer. FIG. 6A is a I-I line sectional view of FIG. 5. FIG. 6B is a II-II line sectional view of FIG. 5. FIG. 6C is a III-III line sectional view of FIG. 5.

Note that the extended state of the diaper 1 refers to a state in which the diaper 1 is extended without creases and a state in which the diaper 1 is extended until dimensions of members (e.g., a sheet for leak-proof walls 21 explained below) configuring the diaper 1 increase to lengths coinciding with or close to dimensions of the members alone. The unfolded state of the diaper 1 refers to a state in which joining of both widthwise side portions 37 of a front waist portion 30a and a back waist portion 30c is released. The widths, lengths, and positions of parts of the diaper 1 are desirably measured and compared in a state in which the diaper 1 is unfolded and extended.

The diaper 1 includes: a substantially rectangular absorbent main body 10; a pair of leak-proof walls 20 provided on the respective widthwise side portions of the absorbent main body 10 and capable of standing on the skin side in the thickness direction; and an exterior body 30. As shown in FIG. 1, the pull-on disposable diaper 1 has an up-down direction and a width direction. As shown in FIG. 2, the absorbent main body 10 and the exterior body 30 have a longitudinal direction, a width direction, and a thickness direction intersecting one another. The width direction of the pull-on disposable diaper 1 correspond to the width directions of the absorbent main body 10 and the exterior body 30. The up-down direction of the pull-on disposable diaper 1 correspond to parts of the longitudinal directions of the absorbent main body 10 and the exterior body 30. The longitudinal direction of the diaper 1 in the unfolded state (FIG. 2) coincides with the longitudinal direction of the absorbent main body 10 and the exterior body 30. A front side in the longitudinal direction is set as a side in contact with the abdomen of the wearer. A back side in the longitudinal direction is set as a side in contact with the buttocks and the back of the wearer.

The exterior body 30 is located on a non-skin side (a side not in contact with the wearer) in the thickness direction of the absorbent main body 10 and is joined and integrated with the absorbent main body 10. The exterior body 30 is formed in a substantial hourglass shape in the unfolded state (FIG. 2) of the diaper 1. The exterior body 30 includes: a substantially rectangular front waist portion 30a and a back waist portion 30c which is elongated in the width direction; and a crotch portion 30b located between both the sections 30a and 30c. The one longitudinal end of the absorbent main body 10 is located in the widthwise central portion of the front waist portion 30a, and the other longitudinal end is located in the widthwise central portion of the back waist portion 30c. Note that a configuration which the crotch portion 30b is not included is also acceptable.

In a manufacturing process of the diaper 1, from the unfolded state in FIG. 2, the absorbent main body 10 and the exterior body 30 are folded into two in the longitudinal central portion thereof such that the front waist portion 30a and the back waist portion 30c overlap. Thereafter, the widthwise side portions 37 of the back waist portion 30c are respectively joined to the widthwise side portions 37 of the front waist portion 30a by means such as welding. Thereby, the diaper 1 is formed into the underpants shape in FIG. 1, forming a waist opening HB and a pair of leg openings HL in the diaper 1.

As shown in FIG. 3, the exterior body 30 includes: a front outer-layer sheet 31a and a front inner-layer sheet 31b forming the front waist portion 30a; a back outer-layer sheet 32a and a back inner-layer sheet 32b forming the back waist portion 30c; and a center sheet 33 forming the crotch portion 30b. As these sheets, spunbond nonwoven fabric, SMS nonwoven fabric, and the like can be illustrated.

A plurality of front elastic members 34 such as elastic strings are provided at intervals in the up-down direction in the front waist portion 30a. The plurality of front elastic members 34 are attached extending along the width direction between the front outer-layer sheet 31a and the front inner-layer sheet 31b. Similarly, a plurality of back elastic members 35 such as elastic strings are provided at intervals in the up-down direction in the back waist portion 30c. The plurality of back elastic members 35 are attached extending along the width direction between the back outer-layer sheet 32a and the back inner-layer sheet 32b. Accordingly, the front waist portion 30a and the back waist portion 30c fit the wearer's waist.

As shown in FIG. 2, a plurality of leg elastic members 36 such as elastic strings are also provided in parts along the leg opening HL of the front waist portion 30a and the back waist portion 30c. The plurality of leg elastic members 36 are attached stretching between the front outer-layer sheet 31a and the front inner-layer sheet 31b and between the back outer-layer sheet 32a and the back inner-layer sheet 32b. Accordingly, the front waist portion 30a and the back waist portion 30c fit the wearer's legs.

The absorbent main body 10 includes a liquid-permeable top sheet 11, a liquid-permeable second sheet 12, an absorbent core 40, a liquid-impermeable back sheet 13, and a crotch-elastic-member cover sheet 14; these elements are provided in order from the skin side (the side in contact with the wearer) in the thickness direction as shown in FIG. 3.

As the top sheet 11, for example, hydrophilic spunbond nonwoven fabric can be illustrated. As the second sheet 12, for example, hydrophilic air-through nonwoven fabric can be illustrated. As the back sheet 13, for example, a polyethylene film can be illustrated. The crotch-elastic-member cover sheet 14 may be either a liquid-permeable sheet or a liquid-impermeable sheet. For example, hydrophobic spunbond nonwoven fabric can be illustrated. Note that the second sheet 12 plays roles of improvement of absorbency, backflow prevention of excrement, and the like by density gradient between the second sheet 12 and the top sheet 11. However, the diaper 1 may have a form not including the second sheet 12.

The absorbent core 40 is a member that absorbs and retains excrement such as urine. The absorbent core 40 is formed of a liquid absorbent fiber such as pulp mixed with high absorbency polymer (SAP). Note that the absorbent core 40 may be covered with a liquid-permeable sheet such as a tissue. The absorbent core 40 has a two-layer structure and includes an upper-layer core 41 and a lower-layer core 42 disposed on the non-skin side in the thickness direction with respect to the upper-layer core 41. The lower-layer core 42 includes a pair of side low-basis-weight portions 43 and a center low-basis-weight portion 44 formed by hollowing the absorbent core 40.

A plurality of crotch elastic members 15 such as elastic strings are provided at widthwise intervals in a part overlapping the central portion in the longitudinal direction and the width direction of the absorbent main body 10, specifically, the center low-basis-weight portion 44 of the absorbent core 40 in a plan view in the thickness direction. The plurality of crotch elastic members 15 are attached extending along the longitudinal direction between the back sheet 13 and the crotch-elastic-member cover sheet 14.

Each of the pair of leak-proof walls 20 includes the leak-proof-wall sheet 21 and a plurality of leak-proof-wall elastic members 22 that stretches/contracts in the longitudinal direction of the absorbent main body 10. The leak-proof-wall sheet 21 may be either a liquid-permeable sheet or a liquid-impermeable sheet. Hydrophobic SMS nonwoven fabric or the like can be illustrated as the leak-proof-wall sheet 21. An elastic string or the like can be illustrated as the leak-proof-wall elastic member 22. As shown in FIG. 6A, each of the pair of leak-proof walls 20 includes a skin-side portion 23 and a non-skin-side portion 24 disposed on the non-skin side in the thickness direction with respect to the skin-side portion 23 (the details thereof will be described later).

As shown in FIG. 2, a plurality of leg elastic members 16 such as elastic strings are provided at widthwise intervals in the longitudinal central portion and on the widthwise side portions of the absorbent main body 10. As shown in FIG. 6C, the plurality of leg elastic members 16 are attached extending along the longitudinal direction between the back sheet 13 and the leak-proof-wall sheet 21. Accordingly, the diaper 1 fits the wearer's legs.

Note that the string-shaped elastic member such as the elastic string is illustrated as the elastic members (the leak-proof-wall elastic member 22, the leg elastic members 16 and 36, the front elastic member 34, and the back elastic member 35) included in the diaper 1. However, the present invention is not limited thereto. A sheet-shaped elastic member may be used.

<Absorbent Core 40 and Leak-Proof Wall 20>

Figure 7:
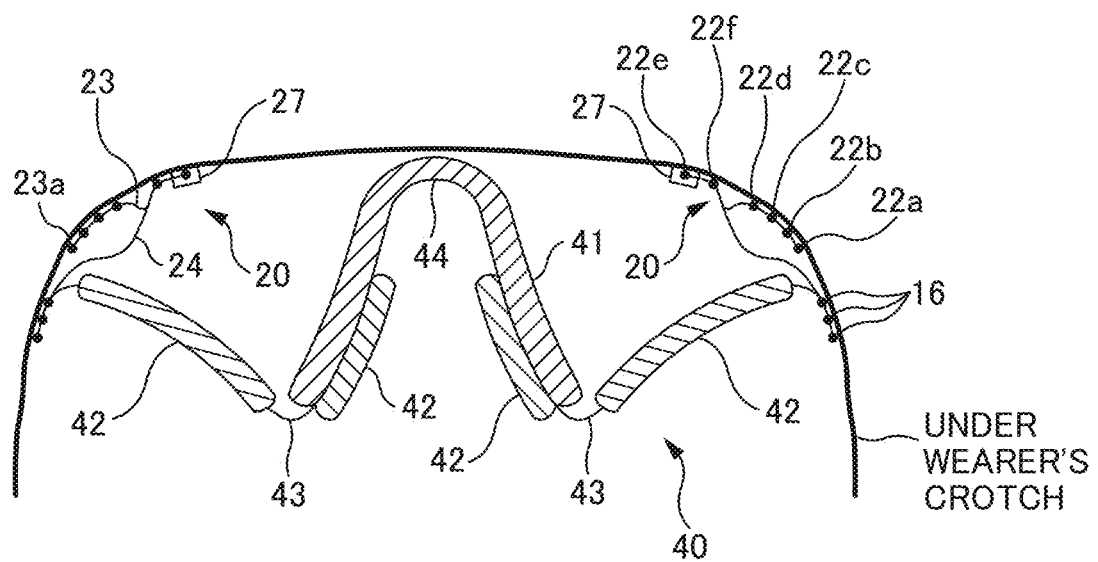
FIG. 7 is a schematic sectional view showing deformation during wearing of an absorbent core and a leak-proof wall.
Figure 8:
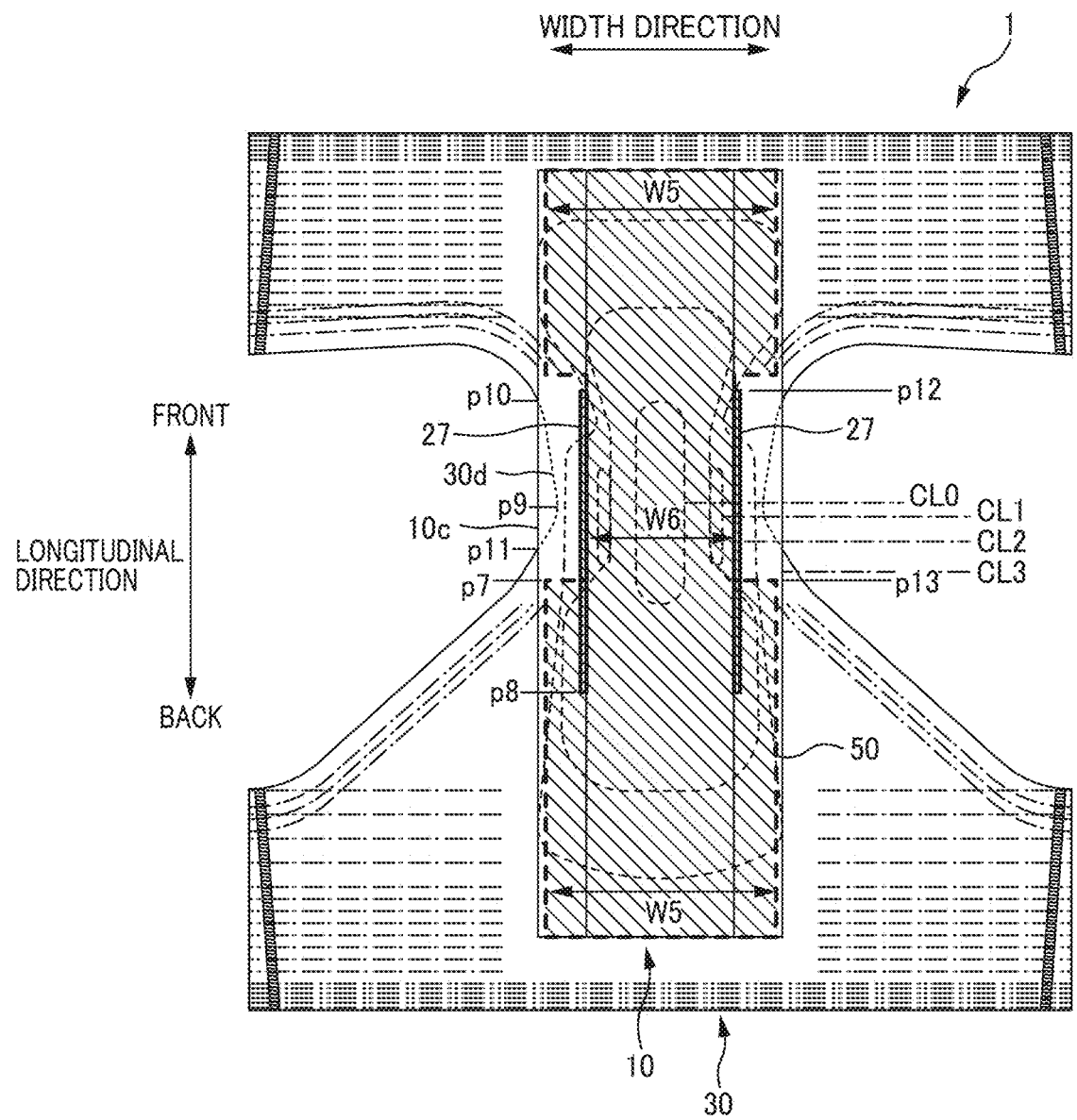
FIG. 8 is a schematic plan view of the diaper in the unfolded and extended state.

FIG. 7 is a schematic sectional view showing deformation of the absorbent core 40 and the leak-proof wall 20 during wearing. To prevent complication of the figure, the top sheet 11 and the like are omitted in FIG. 7. FIG. 8 is a schematic plan view of the diaper 1 in the unfolded and extended state and is a diagram showing a bonding region 50 of the absorbent main body 10 and the exterior body 30.

As explained above, the absorbent core 40 includes the upper-layer core 41 and the lower-layer core 42 disposed on the non-skin side in the thickness direction with respect to the upper-layer core 41. The lower-layer core 42 includes the side low-basis-weight portion 43 (the low-basis-weight portion according to the present invention) in the longitudinal central portion and on the side portion on one widthwise side (e.g., the right side). Also, the lower-layer core 42 includes the side low-basis-weight portion 43 (the low-basis-weight portion according to the present invention) in the longitudinal central portion and the side portion on the other widthwise side (e.g., the left side). The lower-layer core 42 includes the center low-basis-weight portion 44 (the low-basis-weight portion according to the present invention) in the central portion in the longitudinal direction and the width direction. It is assumed that the absorbent core 40 is absent in the pair of side low-basis-weight portions 43 and the center low-basis-weight portion 44. The plane shape of the side low-basis-weight portion 43 and the center low-basis-weight portion 44 is a substantially rectangular shape (a barrel shape) elongated in the longitudinal direction. As shown in FIG. 4, the longitudinal central portion of the upper-layer core 41 is narrowed inward in the width direction. The part of the upper-layer core 41 longitudinally overlapping the side low-basis-weight portion 43 is disposed inside an outer widthwise end 43a of the side low-basis-weight portion 43. In the lower-layer core 42, the part on the front side in the longitudinal direction with respect to the side low-basis-weight portion 43 is narrowed inward in the width direction. The lower-layer core 42 includes, outside the side low-basis-weight portion 43 in the width direction, a part where the absorbent core 40 is present.

Accordingly, in the longitudinal central portion of the absorbent core 40, as shown in the sectional view of FIG. 6C, only the upper-layer core 41 is present in a position where the center low-basis-weight portion 44 is provided, the upper-layer core 41 and the lower-layer core 42 are present between the center low-basis-weight portion 44 and the side low-basis-weight portion 43, the absorbent core 40 is absent in the position where the side low-basis-weight portion 43 is provided, and only the lower-layer core 42 is present outside the side low-basis-weight portion 43 in the width direction.

Accordingly, when the diaper 1 is put on, exerting a the wearer's force for tightening the wearer's thighs from outside to inside in the width direction deforms the longitudinal central portion of the absorbent core 40 as shown in FIG. 7. Specifically, a part where the thin center low-basis-weight portion 44 is provided bends along the longitudinal direction to be convex to the wearer side. A part between the pair of side low-basis-weight portions 43 is deformed in a ridge shape. Parts outside the pair of side low-basis-weight portions 43 in the width direction stand toward the wearer side, from the side low-basis-weight portions 43. That is, the cross section is deformed into a W shape.

Accordingly, the widthwise central portion of the absorbent core 40 comes into close contact with the excretion part of the wearer via the top sheet 11 and the like. The plurality of crotch elastic members 15 are provided in the position where the center low-basis-weight portion 44 is provided. Accordingly, the widthwise central portion of the absorbent core 40 is contracted by the plurality of crotch elastic members 15 and more easily comes into close contact with the excretion part of the wearer. This enables the widthwise central portion of the absorbent core 40 to absorbed excrement without spreading, making the excrement less likely to flow sideward. Even if the excrement is not fully absorbed by the widthwise central portion of the absorbent core 40 and flows sideward, the excrement is dammed by the widthwise side portion of the absorbent core 40 standing in the side low-basis-weight portion 43. This can prevent side leakage of the diaper 1.

Note that the absorbent core 40 may be formed in one-layer structure. However, by forming the absorbent core 40 in the two-layer structure, the center low-basis-weight portion 44 partially recessed in the thickness direction in the widthwise central portion of the absorbent core 40 can be easily formed. The thickness is reduced by making parts outside the side low-basis-weight portion 43 in the width direction one-layered, and absorbency is ensured by making parts inside the side low-basis-weight portions 43 two-layered; this makes it easier for the widthwise side portions of the absorbent core 40 to stand.

Further, as shown in FIG. 4, an outer widthwise side end 12a of the second sheet 12 coincides with an inner widthwise side end 43b of the side low-basis-weight portion 43. Accordingly, in the absorbent main body 10, a difference in thickness (a rigidity difference) between the widthwise sides increases on opposite sides of the side low-basis-weight portion 43, making it easier for the widthwise side portion of the absorbent core 40 to stand.

In the side low-basis-weight portion 43, it is preferable that the top sheet 11 and the back sheet 13 are pasted together and fixed. Consequently, the absorbent core 40 is prevented from bending in an unintended position. The absorbent core 40 is easily deformed as shown in FIG. 7.

In this embodiment, the absorbent core 40 is absent in the pair of side low-basis-weight portions 43 and the center low-basis-weight portion 44 (i.e., a basis weight is set to zero). However, the present invention is not limited thereto. In the pair of side low-basis-weight portions 43 and the center low-basis-weight portion 44, the absorbent core 40 of a basis weight lower than that in the surrounding may be present. In that case as well, the absorbent core 40 can be deformed as shown in FIG. 7. Note that comparison of basis weights between the side low-basis-weight portion 43 and the surrounding thereof only has to be performed by a well-known method. For example, the basis weights may be visually compared. A target part may be cut out from the diaper 1 and a value (g/cm²) obtained by dividing masses of the sections by areas may be calculated and compared.

As explained above, the pair of leak-proof walls 20 is provided extending along the longitudinal direction on the widthwise side portions of the absorbent main body 10. Each of the pair of leak-proof walls 20 includes the skin-side portion 23 and the non-skin-side portion 24. As shown in FIG. 4, both longitudinal ends 21a of the leak-proof-wall sheet 21 forming the leak-proof walls 20 coincides with both longitudinal ends 10a of the absorbent main body 10.

A fixed end portion 21b, which is one widthwise end portion of the leak-proof-wall sheet 21, is fixed between the back sheet 13 and the exterior body 30 as shown in FIG. 6. A free end portion, which is the other end portion in the width direction of the leak-proof-wall sheet 21, is folded back onto a skin-side surface of the top sheet 11 to form the skin-side portion 23 and the non-skin-side portion 24. Specifically, in the manufacturing process of the diaper 1, the free end portion of the leak-proof-wall sheet 21 is folded back to the skin side in the thickness direction in a folding position f1 shown in FIG. 6A, thereafter folded back to the non-skin side in the thickness direction in a folding position f2, thereafter folded back to the skin side in the thickness direction in a folding position f3, and provided on the skin-side surface of the top sheet 11. A section between the folding positions f1 and f2 is the skin-side portion 23. A section between the folding positions f2 and f3 is the non-skin-side portion 24. Note that, in this embodiment, the skin-side portion 23 and the non-skin-side portion 24 are formed by one leak-proof-wall sheet 21. However, the present invention is not limited thereto. For example, a skin-side portion and a non-skin-side portion may be formed of separate sheets (separate members).

As shown in FIG. 6, each of the skin-side portion 23 and the non-skin-side portion 24 is formed by two layers of the leak-proof-wall sheet 21. Four leak-proof-wall elastic members 22a to 22d are attached extending in the longitudinal direction between two layers of leak-proof-wall sheets 21c and 21d of the skin-side portion 23. The four leak-proof-wall elastic members 22a to 22d are disposed at widthwise intervals, sequentially from a widthwise outer side end 23a of the skin-side portion 23, and close to the widthwise outside. Two leak-proof-wall elastic members 22e and 22f are attached extending in the longitudinal direction between two layers of leak-proof-wall sheets 21e and 21f of the non-skin-side portion 24. The two leak-proof-wall elastic members 22e and 22f are disposed at widthwise intervals, sequentially from an inner widthwise side end 24a of the non-skin-side portion 24, and close to widthwise inside.

As shown in FIG. 5 and FIG. 6A, end joined parts 25 are respectively formed at both longitudinal end portions of the leak-proof walls 20. Each of the end joined parts 25 includes: a first end joined part 25a in which the non-skin-side surface of the skin-side portion 23 is joined to the skin-side surface of the non-skin-side portion 24; and a second end joined part 25b in which the non-skin-side surface of the non-skin-side portion 24 is joined to the skin-side surface of the top sheet 11. The first end joined part 25a and the second end joined part 25b are formed over a wide range of the leak-proof wall 20. As shown in FIG. 6B and FIG. 6C, a side joined part 26 is formed in the outer widthwise side portion of the leak-proof wall 20 and between a pair of end joined parts 25 in the longitudinal direction (not shown in FIG. 5); the side joined part 26 is formed in which the non-skin-side surface of the non-skin-side portion 24 and the skin-side surface of the top sheet 11 are joined. Accordingly, in the leak-proof wall 20, a part longitudinally between the pair of end joined parts 25 stands toward the wearer side, from the side joined part 26 by a contracting force of the leak-proof-wall elastic member 22.

Note that the leak-proof wall 20 may have a form not including the side joined part 26. In that case, the leak-proof wall 20 stands on the widthwise side end of the absorbent core 40 or stands on the widthwise side end of the bonding region 50 (see FIG. 8) of a non-skin-side surface of the absorbent main body 10 and a skin-side surface of the exterior body 30. In that case, a standing height of the leak-proof wall 20 can be higher than in the case where the side joined part 26 is provided as explained above. A fixed end portion of the leak-proof-wall sheet 21 may be provided at the side end portion of the skin-side surface of the top sheet 11. The side joined part 26 may be provided and defined as base point of the standing.

As shown in FIG. 6C, the diaper 1 includes a pinching-joined part 27 which is formed by joining at least partially a surface of the skin-side portion 23 and a surface of the non-skin-side portion 24, the surfaces facing to each other (the non-skin-side surface of the skin-side portion 23 and the skin-side surface of the non-skin-side portion 24). As shown in FIG. 5, the pinching-joined part 27 extends along the longitudinal direction and provided inside the distal end (the free end) 23a of the leak-proof wall 20 in the width direction. Note that the width of the pinching-joined part 27 is smaller than the width of the end joined part 25. The skin-side portion 23 includes a part separable from the non-skin-section 24. In this embodiment, as shown in FIG. 6, the pinching-joined part 27 is formed along the inner widthwise side end 24a of the non-skin-side portion 24 (the folding position f2). However, the present invention is not limited thereto. It is sufficient that the pinching-joined part 27 is provided inside the distal end 23a of the leak-proof wall 20 in the width direction. That is, it is sufficient that the pinching-joined part 27 is provided between the distal end 23a of the leak-proof wall 20 and the inner side end 24a of the non-skin-side portion 24. For example, the pinching-joined part 27 may be provided apart from the inner side end 24a of the non-skin-side portion 24 and outside of the inner side end 24a in the width direction.

Consequently, for example, even when a wearer's leg passes through the leg opening HL, the leak-proof-wall sheet 21 is maintained folded. Accordingly, as shown in FIG. 7, the non-skin-side portion 24 stands toward the wearer side, enabling the skin-side portion 23 to come into close surface-to-surface contact with the crotch of the wearer. This makes it possible to improve contact compared with when, for example, the leak-proof wall is linearly in close contact with the wearer. In particular, in the pinching-joined part 27, the skin-side portion 23 and the non-skin-side portion 24 are stacked and an adhesive or the like is applied to the skin-side portion 23 and the non-skin-side portion 24. Accordingly, the pinching-joined part 27 has high rigidity and it is easy to maintain the surface shape of the pinching-joined part 27. This makes it possible to bring the skin-side portion 23 (in particular, the pinching-joined part 27) into close surface-to-surface contact with the crotch part of the wearer, preventing side leakage.

As shown in FIG. 2, the pinching-joined part 27 is disposed extending from a longitudinal central part 1b to a back part 1c of the diaper 1 (in other words, disposed in a position where a part of the crotch portion 30b overlaps longitudinally a part of the back waist portion 30c of the exterior body 30). A part of the pinching-joined part 27, the entire side low-basis-weight portion 43, and the entire center low-basis-weight portion 44 overlap in the longitudinal direction. Thus, it is desirable that the pinching-joined part 27, the side low-basis-weight portion 43, and the center low-basis-weight portion 44 at least partially overlap one another in the longitudinal direction in the unfolded and extended state of the diaper 1 (e.g., FIG. 2). Further, it is desirable that the pinching-joined part 27 is disposed outside the side low-basis-weight portion 43 in the width direction.

Consequently, the part of the absorbent core 40 where the center low-basis-weight portion 44 is provided is brought into close contact with the excretion part of the wearer by the crotch elastic member 15. Further, the skin-side portion 23 (in particular, the pinching-joined part 27) comes into close surface-to-surface contact with the wearer on the outer side in the width direction. This makes the absorbent core 40 absorb excrement without being spread. And, excrement which remains without being absorbed and flows sideward is dammed by the leak-proof wall 20, more reliably preventing side leakage.

The part of the leak-proof wall 20 where the pinching-joined part 27 is provided is supported by the side portion of the absorbent core 40, the side portion standing on the side low-basis-weight portion 43. This makes it possible for the pinching-joined part 27 to securely lifted to the wearer side and to enter the wearer's groin, maintaining close surface-to-surface contact of the skin-side portion 23 (in particular, the pinching-joined part 27) with the wearer. Consequently, side leakage is more surely prevented.

Besides, by providing the pinching-joined part 27, the height of the leak-proof wall 20 standing is the height of the non-skin-side portion 24, which is relatively low. Accordingly, even if the absorbent core 40 absorbs excrement and increases in weight, reducing a droop of the absorbent core 40. Consequently, discomfort is less easily given to the wearer. In particular, the plurality of leak-proof-wall elastic members 22a to 22f in the leak-proof wall 21 increases contact of the skin-side portion 23 with the wearer, making it possible to further prevent the droop of the absorbent core 40. In addition, it is possible to prevent the droop of the absorbent core 40 by the leg elastic member 16 provided at the fixed end portion 21b of the leak-proof wall 20, assisting contact of the skin-side portion 23 with the wearer.

Note that the pinching-joined part 27, the end joined part 25, and the side joined part 26 only have to be joined by a well-known method. For example, joining by application of an adhesive such as hot-melt adhesive, compression bonding, thermal welding, and ultrasonic welding can be illustrated. The skin-side portion 23 and the non-skin-side portion 24 may be joined in the entire region of the pinching-joined part 27 indicated by hatching in FIG. 2 and the like. The skin-side portion 23 and the non-skin-side portion 24 may be partially joined in the pinching-joined part 27 indicated by hatching. A plurality of pinching-joined parts 27 may be provided at intervals in the longitudinal direction with respect to one leak-proof wall 20.

The absorbent core 40 in this embodiment includes, as shown in FIG. 2, the pair of side low-basis-weight portions 43, the center low-basis-weight portion 44, and the crotch elastic member 15. However, the present invention is not limited thereto. For example, the absorbent core 40 may have a form including the pair of side low-basis-weight portions 43 but not including the center low-basis-weight portion 44 and the crotch elastic member 15. In that case, the widthwise central portion of the absorbent core 40 is not in close contact with the wearer. The cross section of the absorbent core 40 is deformed into a cup shape (a concave shape). When the cross section is deformed into the cup shape as well, the leak-proof wall 20 is supported by the standing side portion of the absorbent core 40 while excrement is received by a space portion of a cup. Accordingly, the skin-side portion 23 (in particular, the pinching-joined part 27) is in close surface-to-surface contact with the wearer. Side leakage is prevented. The absorbent core 40 may have a form including the center low-basis-weight portion 44 and the crotch elastic member 15 but not including the pair of side low-basis-weight portions 43. In that case as well, the cross section of the absorbent core 40 is easily deformed into a convex shape. The absorbent core 40 may have a form including the center low-basis-weight portion 44 but not including the crotch elastic member 15 and the pair of side low-basis-weight portions 43. In that case as well, since the center low-basis-weight portion 44 is provided in the lower-layer core 42, the cross section of the absorbent core 40 is easily deformed into a convex shape.

The configuration in which the absorbent core 40 only includes the side low-basis-weight portion 43 on one widthwise side portion is also acceptable; that is, the configuration in which a side low-basis-weight portion 43 is not included on the other widthwise side and in which the center low-basis-weight portion 44 and the crotch elastic member 15 are not included. However, it is more preferable to provide the side low-basis-weight portions 43 on the respective widthwise side portions of the absorbent core 40. Consequently, both of the pair of leak-proof walls 20 can be supported by the side portions of the absorbent core 40 and can be brought in close contact with the wearer. Accordingly, side leakage can be prevented on the widthwise sides.

The non-skin-side portion 24 of the leak-proof wall 20 is folded back inwardly in the width direction at the folding position f3. The skin-side portion 23 is folded back outwardly in the width direction in the folding position f2. The free widthwise end of the skin-side portion 23 is located on the outer side. Accordingly, when a wearer's leg passes through the leg opening HL, the skin-side portion 23 is spread outwardly by the wearer's thigh, making it more easier to bring the skin-side portion 23 into close surface-to-surface contact with the wearer. Since the non-skin-side portion 24 is pulled outwardly by the skin-side portion 23, the non-skin-side portion 24 is less likely to fall inwardly and can securely stand. Since the skin-side portion 23 is pulled inwardly by the non-skin-side portion 24, it is possible to prevent the skin-side portion 23 from excessively spreading outside and protruding beyond the leg opening HL.

In the unfolded and extended state (e.g., FIG. 2) of the diaper 1, the pinching-joined part 27 is disposed inside an outermost widthwise end 40a in a part (p1 to p2 in FIG. 5) of the absorbent core 40 where the side low-basis-weight portion 43 and the center low-basis-weight portion 44 are provided. That is, the part (p1 to p2) of the pinching-joined part 27 longitudinally overlapping the side low-basis-weight portion 43 is located on the absorbent core 40. Accordingly, the leak-proof wall 20 is more stably supported by the side portion of the absorbent core 40 standing from the side low-basis-weight portion 43. This makes it easier to maintain close surface-to-surface contact of the skin-side portion 23 (in particular, the pinching-joined part 27) with the wearer, preventing side leakage.

That the absorbent core 40 is located outside the pinching-joined part 27 in the width direction means that the width of the side portion of the absorbent core 40 standing on the side low-basis-weight portion 43 is relatively long. Accordingly, the side portion of the absorbent core 40 easily bends along the wearer's crotch. The fitness of the absorbent core 40 is improved. However, the present invention is not limited thereto. The pinching-joined part 27 may be disposed outside the outer widthwise side end 40a of the absorbent core 40.

As shown in FIG. 6B, the two leak-proof-wall elastic members 22e and 22f are disposed on and in the vicinity of the inner widthwise side portions of the skin-side portion 23 and the non-skin-side portion 24; the inner widthwise side portions correspond to positions where the skin-side portion 23 and the non-skin-side portion 24 overlap the pinching-joined part 27 in the width direction. Accordingly, the pinching-joined part 27 can securely come into close surface-to-surface contact with the wearer's groin, preventing side leakage. The leak-proof-wall elastic member 22f is provided in the non-skin-side portion 24 and at a position near the pinching-joined part 27. This enables the non-skin-side portion 24 to securely push up the pinching-joined part 27 and to bring the pinching-joined part 27 into close contact with the wearer.

As shown in FIG. 6C, the four leak-proof-wall elastic members 22a to 22d are disposed in the part of the skin-side portion 23 other than the pinching-joined part 27 (hereinafter referred to as a skin-side single portion 23b as well). Accordingly, the skin-side single portion 23b having lower rigidity than the pinching-joined part 27 securely comes into close surface-to-surface contact with the wearer while being deformed along the wearer's crotch. A contact force of the skin-side single portion 23b (i.e., a contracting force of the leak-proof-wall elastic member 22) necessary for preventing side leakage is realized by the plurality of leak-proof-wall elastic members 22a to 22d. This makes it possible to prevent local contact of the skin-side single portion 23b, improving the wearer's feeling of the diaper 1. However, the present invention is not limited thereto. It is sufficient that at least one leak-proof-wall elastic member 22 is provided in the leak-proof wall 20.

Of the leak-proof-wall elastic member 22 and the leg elastic members 16 and 36 explained above, the figures show only parts that develop stretchability. Accordingly, parts of elastic members that do not develop stretchability may be present on the longitudinal outer side of the elastic members shown in the figures. As shown in FIG. 5, longitudinal ends (black circles) of the parts of the leak-proof-wall elastic member 22 that develop stretchability are located outside a longitudinal end 27a of the pinching-joined part 27. That is, stretching/contracting force of the leak-proof-wall elastic member 22 acts on the entire longitudinal region of the pinching-joined part 27. Accordingly, the pinching-joined part 27 is in close contact with the wearer over the entire longitudinal region.

It is desirable that a longitudinal stretching/contracting force per unit width in the width direction on a side portion 20A of the inner widthwise side of the skin-side portion 23 and the non-skin-side portion 24 is equal to or larger than a longitudinal stretching/contracting force per unit width in the width direction of a side portion 20B of the outer widthwise side of the skin-side portion 23. In the present embodiment, as shown in FIG. 6B, a widthwise part where the two leak-proof-wall elastic members 22e and 22f are provided around the pinching-joined part 27 is defined as "the inner widthwise side portion 20A of the skin-side portion 23 and the non-skin-side portion 24 (hereinafter also referred to as an inner side portion)", and a widthwise part where the four leak-proof-wall elastic members 22a to 22d of the skin-side single portion 23b are provided is defined as "the outer widthwise side portion 20B of the skin-side portion 23 (hereinafter also referred to as an outer side portion)". However, the present invention is not limited thereto. For example, among regions obtained by dividing the skin-side portion 23 or the non-skin-side portion 24 into two or three, an inner widthwise side region may be defined as "an inner side portion" and an outer widthwise side region may be defined as "an outer side portion". As in the present embodiment, the widthwise lengths of the inner side portion and the outer side portion may be different, and also may be identical.

Specifically, the two leak-proof-wall elastic members 22e and 22f are disposed on the inner side portion 20A, and these elastic members 22e and 22f have a diameter of 620 dtex, rate of stretch of 2.4, and the longitudinal length for developing stretchability (so-called effective length) of 560 mm. The four leak-proof-wall elastic members 22a to 22d are disposed on the outer side portion 20B, and these elastic members 22a to 22d have a diameter of 470 dtex, the rate of stretch of 2.3, and an effective length of 510 mm. Note that the rate of stretch indicates the degree of stretch assuming that the natural length of the elastic member is 1. For example, when the rate of stretch is 2.4, the elastic member is fixed to a sheet or the like, with extending from the natural length to 2.4 times of the natural length. With this configuration, in this embodiment, the longitudinal stretching/contracting force per unit width of the inner side portion 20A is larger than the longitudinal stretching/contracting force per unit width of the outer side portion 20B.

This makes it possible to securely bring the pinching-joined part 27 into close contact with the wearer's groin by the high stretching/contracting force of the inner side portion 20A. Reducing the stretching/contracting force of the outer side portion 20B makes it possible to prevent the skin-side portion 23 from returning or falling inwardly. Accordingly, the skin-side portion 23 can be brought into close surface-to-surface contact with the wearer.

Note that the configuration of the leak-proof-wall elastic member 22 is not limited to the foregoing configuration. The stretching/contracting force can increased by increasing the diameter of the leak-proof-wall elastic member 22, by increasing the rate of stretch of the leak-proof-wall elastic member 22, by increasing the effective length of the leak-proof-wall elastic member 22, and by increasing the number of the leak-proof-wall elastic members 22 per unit width. Accordingly, it is preferable that the stretching/contracting force per unit width of the inner side portion 20A is equal to or larger than the stretching/contracting force per unit width of the outer side portion 20B as follow: making different at least one of the diameter, the rate of stretch, the effective length, and the disposed number of the leak-proof-wall elastic members 22, between the inner side portion 20A and the outer side portion 20B. The leak-proof-wall elastic members 22e and 22f of the inner side portion 20A may be provided in the skin-side portion 23.

It is sufficient that comparison of the stretching/contracting forces of the inner side portion 20A and the outer side portion 20B is performed by a well-known method. For example, cut out the inner side portion 20A and the outer side portion 20B from the diaper 1 as samples. The length of the samples is a length including the entire range of the effective length of the leak-proof-wall elastic member 22. Hold both end portions of the samples in a direction of pulling (the longitudinal direction of the diaper 1) between chucks of a tensile test machine such as Autograph (AGS-G100N) manufactured by SHIMADZU Corporation. For each of the cut-out samples, obtain a load (N) in a state in which the chucks are separated and the samples are extended; obtain for example, a load during maximum tension and a load halfway in tension or halfway in return.

Note that an initial inter-chuck distance is recommended to be shorter than the length of a shrunk-up effective length portion of the leak-proof-wall elastic member 22. Besides, tensile speed and the like can be set arbitrarily. Convert the load (a measurement value) obtained for each of the cut-out samples into a value per unit width (e.g., 1 cm). For example, assuming the case where four leak-proof-wall elastic members 22 are included in a sample cut out at 25 mm width, the width B of a region where the four leak-proof-wall elastic members 22 are provided (an interval B of the outer elastic members) is 15 mm, and the measurement value is A. In this case, a stretching/contracting force X per unit width is $X = A \times 10/B = A \times 10/15$ (N/cm). Note that, if the interval of the outer elastic members is different depending on a longitudinal position, it is desirable to calculate a rough average of intervals and use the average for calculation. In the case where the leak-proof-wall elastic member 22 is sheet-shaped, it is desirable to substitute the width B of the sheet-shaped elastic member instead of the interval B of the outer elastic members and calculate the stretching/contracting force. It should be noted that samples have to be cut out such that an elastic member other than a target elastic member is not included in the samples.

As shown in FIG. 5, it is preferable that the longitudinal length of the first end joined part 25a of the upper layer is larger than the longitudinal length of the second end joined part 25b of the lower layer. Consequently, the effective length of the leak-proof-wall elastic members 22e and 22f disposed on the inner side portion 20A can be larger than the effective length of the leak-proof-wall elastic members 22a to 22d disposed on the outer side portion 20B. The skin-side portion 23 is securely fixed by the long, first end joined part 25a, making it easier to maintain a state of a surface facing the outer side. On the contrary, the non-skin-side portion 24 is easily standing from the short second end joined part 25b.

The end joined part 25 is not provided on extended lines of the leak-proof-wall elastic members 22e and 22f. The inner side portion 20A is separated from the top sheet 11. Accordingly, a contracting force of the leak-proof-wall elastic members 22e and 22f is less likely to be transmitted to the longitudinal end portion of the absorbent main body 10. This can prevent deterioration in appearance and in absorption caused by contraction of the longitudinal end portion.

In the unfolded and extended state (e.g., FIG. 8) of the diaper 1, the longitudinal center CL0 of the center low-basis-weight portion 44, the longitudinal center CL1 of the side low-basis-weight portion 43, and the longitudinal center CL2 of the pinching-joined part 27 are located on the front side with respect to the longitudinal center CL3 of the diaper 1 (hereinafter referred to as product center as well). That is, the center low-basis-weight portion 44, the side low-basis-weight portion 43, and the pinching-joined part 27 are formed on the longitudinally front side with respect to the product center CL3. The diaper 1 has a region which comes into contact with an excretion part where the wearer excretes urine (that is, a region where side leakage easily occurs), and in that region, the widthwise central portion of the absorbent core 40 is brought into close contact with the excretion part. The widthwise side portion of the absorbent core 40 stands on the side low-basis-weight portion 43 and supports the leak-proof wall 20. The skin-side portion 23 (in particular, the pinching-joined part 27) comes into close contact with the wearer. Accordingly, side leakage is more surely prevented. However, the present invention is not limited thereto. The longitudinal centers of the center low-basis-weight portion 44, the side low-basis-weight portion 43, and the pinching-joined part 27 may be located in or behind the product center CL3.

In the unfolded and extended state (e.g., FIG. 2) of the diaper 1, as shown in FIG. 5, the longitudinal length L1 of the pinching-joined part 27 is larger than the longitudinal length L2 of the side low-basis-weight portion 43 and the longitudinal length L3 of the center low-basis-weight portion 44. Accordingly, the skin-side portion 23 (in particular, the pinching-joined part 27) is in close contact with the wearer over a wide longitudinal range, preventing side leakage. Thus, the following configuration is preferable: the side low-basis-weight portion 43 and the center low-basis-weight portion 44 are not unnecessarily long; the side low-basis-weight portion 43 and the center low-basis-weight portion 44 are not provided in the front and back longitudinal portions of the absorbent core 40; and the side and central portions in the width direction do not stand. Consequently, the front and back portions of the absorbent core 40 are formed in surface shapes conforming to the abdomen and the buttocks of the wearer. This improves fitness of the diaper 1. However, the present invention is not limited thereto. The length of the pinching-joined part 27 may be smaller than the length of the side low-basis-weight portion 43 and the center low-basis-weight portion 44.

In the unfolded and extended state (e.g., FIG. 2) of the diaper 1, as shown in FIG. 5, the longitudinal back end portion of the pinching-joined part 27 is located on the back side in the longitudinal direction with respect to the side low-basis-weight portion 43 and the center low-basis-weight portion 44. Accordingly, as explained above, the widthwise side portion and the widthwise central portion do not stand in the back portion of the absorbent core 40. The back portion of the absorbent core 40 fits the buttocks of the wearer. Further, the longitudinal back end portion of the pinching-joined part 27 is not pushed up by the widthwise side portion of the absorbent core 40. Accordingly, on the back side with respect to the side low-basis-weight portion 43, it is desirable to increase the width of the upper-layer core 41. Also, it is desirable that the back end portion of the pinching-joined part 27 (p3 to p4 in FIG. 5) is placed on the upper-layer core 41 and the lower-layer core 42 in the thickness direction. Consequently, the back end portion of the pinching-joined part 27 is pushed up by two layers of the absorbent core 40 and can come into close contact with the wearer.

In the front and back longitudinal portions of the diaper 1, momentum of excrement (urine) decreases, and the risk of side leakage is low. Accordingly, in the diaper 1, in the longitudinal end portions of the leak-proof wall 20, the pinching-joined part 27 is not provided. Absence of the pinching-joined part 27 in the part where the risk of side leakage is low and softening the leak-proof wall 20 as mentioned above make it possible to improve wearer's feeling of the diaper 1. The skin-side portion 23 as well as the non-skin-side portion 24 are capable of standing at the longitudinal end portions of the leak-proof wall 20, increasing the height of the leak-proof wall. This makes it possible for the leak-proof wall 20 to wrap the buttocks and the abdomen of a plump wearer. However, the present invention is not limited thereto. The pinching-joined part 27 may be provided at the longitudinal end portions of the leak-proof wall 20. In that case, the width of the pinching-joined part 27 may have a smaller width at set smaller the longitudinal end portions of the leak-proof wall 20 than the width at the central portion of the leak-proof wall 20. In this case, the same effect can be obtained.

In the unfolded and extended state (e.g., FIG. 2) of the diaper 1, as shown in FIG. 5 and FIG. 6C, the widthwise length W1 of the side low-basis-weight portion 43 is larger than the widthwise length W2 of the pinching-joined part 27. This ensures, in the side low-basis-weight portion 43, an extension margin of the back sheet 13 and the like in the lower layer of the absorbent core 40 necessary for the side portion of the absorbent core 40 to stand. Accordingly, the side portion of the absorbent core 40 easily stands and easily supports the leak-proof wall 20. On the other hand, reducing the width of the pinching-joined part 27 reduces a downward force on the pinching-joined part 27 received from the wearer, preventing the non-skin-section 24 from being hindered to stand. Accordingly, the non-skin-side portion 24 can dam excrement and can push up the skin-side portion 23 and bring the skin-side portion 23 into close contact with the wearer. However, the present invention is not limited thereto. The width of the pinching-joined part 27 may be equal to or larger than the width of the side low-basis-weight portion 43.

The widthwise length W7 of the center low-basis-weight portion 44 is larger than the widthwise length W2 of the pinching-joined part 27. This increases the width of the absorbent core 40 which is to be in close contact with the wearer by the center low-basis-weight portion 44. Excrement is securely spot-absorbed.

In the unfolded and extended state (e.g., FIG. 2) of the diaper 1, as shown in FIG. 6C, the widthwise length W3 of the non-skin-side portion 24 is larger than the widthwise length W4 of the skin-side portion 23. This ensures the height of the standing of the non-skin-side portion 24. On the other hand, reducing the width of the skin-side portion 23 reduces a downward force on the skin-side portion 23 received from the wearer, preventing the non-skin-section 24 from being hindered to stand. Accordingly, the non-skin-side portion 24 can dam excrement and can push up the skin-side portion 23 and bring the skin-side portion 23 into close contact with the wearer. However, the present invention is not limited thereto. The width of the skin-side portion 23 may be equal to or larger than the width of the non-skin-side portion 24.

As shown in FIG. 2, in the unfolded and extended state of the diaper 1, a back longitudinal end portion (p5 to p6) of the pinching-joined part 27 longitudinally overlaps the leg elastic member 36 of the back waist portion 30c. Thus, it is preferable that at least one end portion of the pinching-joined part 27 overlaps the leg elastic member 36 of the front waist portion 30a or the back waist portion 30c. Consequently, when the diaper 1 is put on, the part of the leak-proof wall 20 where the pinching-joined part 27 is provided is pulled obliquely upward by the leg elastic member 36. This makes it easier to maintain close contact of the pinching-joined part 27 with the wearer. The non-skin-side portion 24 also easily stands, and therefore the non-skin-side portion 24 dams excrement. The skin-side portion 23 is pushed up, coming into close contact with the wearer.

The non-skin-side surface of the absorbent main body 10 and the skin-side surface of the exterior body 30 are bonded with an adhesive or the like in the bonding region 50 (a region surrounded by a thick dotted line) shown in FIG. 8. In the unfolded and extended state (e.g., FIG. 8) of the diaper 1, a back end portion (p7 to p8) of the pinching-joined part 27 longitudinally overlaps the bonding region 50. Thus, it is preferable that, in the longitudinal direction, at least one end portion of the pinching-joined part 27 overlaps the bonding region 50. Consequently, when the diaper 1 is put on, the part of the leak-proof wall 20 where the pinching-joined part 27 is provided is pulled obliquely upward by the exterior body 30. Accordingly, close contact of the pinching-joined part 27 with the wearer is easily maintained. The non-skin-side portion 24 also easily stands, and therefore the non-skin-side portion 24 dams excrement. The skin-side portion 23 is pushed up, coming into close contact with the wearer.

The longitudinal central portion of the exterior body 30 (the crotch portion 30b) is narrowed inward in the width direction. As shown in FIG. 8, the narrowest position p9 of the exterior body 30 is located on the front side in the longitudinal direction with respect to the product center CL3 and corresponds to the crotch part of the wearer. Accordingly, even when the wearer closes the legs, a twist of the diaper 1 can be reduced, making it possible to improve wearer's feeling of the diaper 1. The width of the exterior body 30 increases from a position on the front side in the longitudinal direction with respect to the product center CL3, making it possible for the exterior body 30 to wrap the buttocks of the wearer.

In the unfolded and extended state (e.g., FIG. 8) of the diaper 1, the absorbent main body 10 includes a part (p10 to p11) having a larger width than that of the exterior body 30, in a region in which the absorbent main body 10 longitudinally overlaps the pinching-joined part 27. That is, in the longitudinal central portion of the absorbent main body 10, an outer widthwise side end 10c of the absorbent main body 10 is located outside an outer widthwise side end 30d of the exterior body 30. This makes it possible to prevent the leak-proof wall 20 from being covered with the exterior body 30 in the region where the pinching-joined part 27 is provided. This enables the skin-side portion 23 of the leak-proof wall 20 to come into close surface-to-surface contact with the wearer while being opened by a wearer's leg at the time of putting on the diaper.

As shown in FIG. 8, the bonding region 50 where the absorbent main body 10 and the exterior body 30 are bonded is narrowed in the longitudinal central portion. The width W6 in the longitudinal central portion is smaller than the width W5 at the longitudinal end portion. Thus, in the unfolded and extended state (e.g., FIG. 8) of the diaper 1, it is preferable that the bonding region 50 includes a part (p12 to p13) having a smaller width than that of the longitudinal end portions, in a region in which the bonding region 50 longitudinally overlaps the pinching-joined part 27. Accordingly, the widthwise side portion of the exterior body 30 longitudinally overlapping the pinching-joined part 27 can be separated from the absorbent main body 10. The part of the exterior body 30 separated from the absorbent main body 10 has flexibility, making the part more likely to be tucked. Creases easily occur in the part because of the influence of the leg elastic member 36 and the like. This makes it possible to prevent the leak-proof wall 20 from being covered with the exterior body 30 in the region where the pinching-joined part 27 is provided. This enables the skin-side portion 23 of the leak-proof wall 20 to come into close surface-to-surface contact with the wearer while being opened by a wearer's leg at the time of putting on the diaper.

Thus, it is preferable that, in an appearance of the pull-on disposable diaper 1 from the front waist portion 30a side as shown in FIG. 1, at least a part of the leak-proof wall 20 in a lower end region 1d in the up-down direction is exposed from the exterior body 30 in the width direction (outwardly). Consequently, as explained above, the leak-proof wall 20 is not covered with the exterior body 30, and it becomes possible for the skin-side portion 23 to come into close surface-to-surface contact with the wearer while being opened by a wearer's leg at the time of putting on the diaper.

This makes it possible to prevent side leakage. Also, it is possible to prevent the wearer's legs from being caught by the exterior body 30 at the time of putting on the diaper. This makes it easier to put on the diaper 1. Since the leak-proof wall 20 is visually recognized from the leg opening HL, it is possible to give to the wearer a safe impression that a leak less easily occurs. Besides, the position of the leg opening HL is easily seen because of the exposed leak-proof wall 20. A caregiver or the like can easily put the diaper 1 on the wearer.

The present invention is not limited thereto. It is acceptable that the width of the bonding region 50 where the absorbent main body 10 and the exterior body 30 are bonded is uniform. In FIG. 8, the bonding region 50 is continuously provided over the entire region from one longitudinal end to the other longitudinal end of the absorbent main body 10. However, the present invention is not limited thereto. For example, the bonding region 50 may be discontinuously provided in the longitudinal direction.

Second Embodiment

Figure 9:
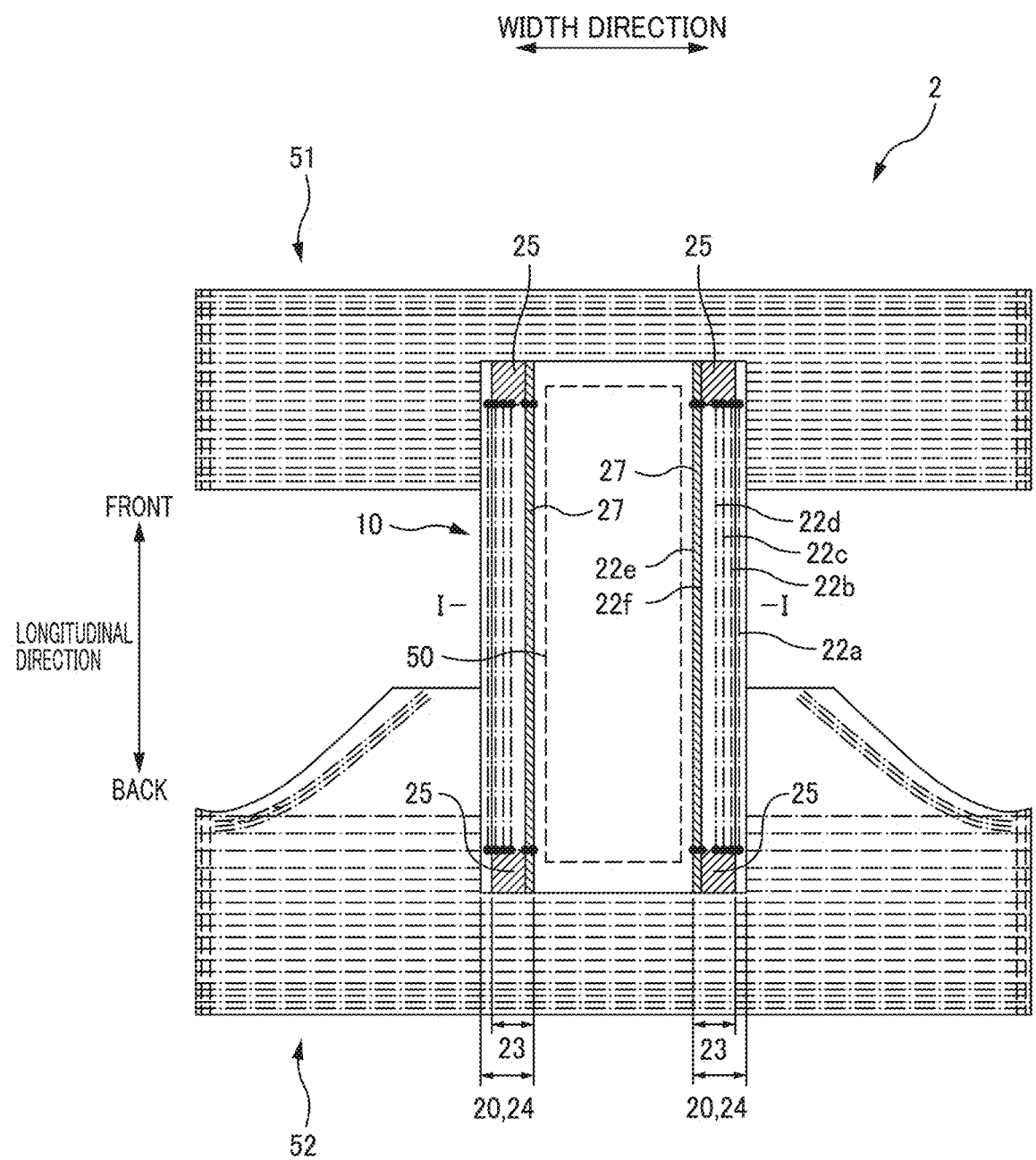
FIG. 9 is a schematic plan view of a diaper 2 in a second embodiment in an unfolded and extended state.
Figure 10:
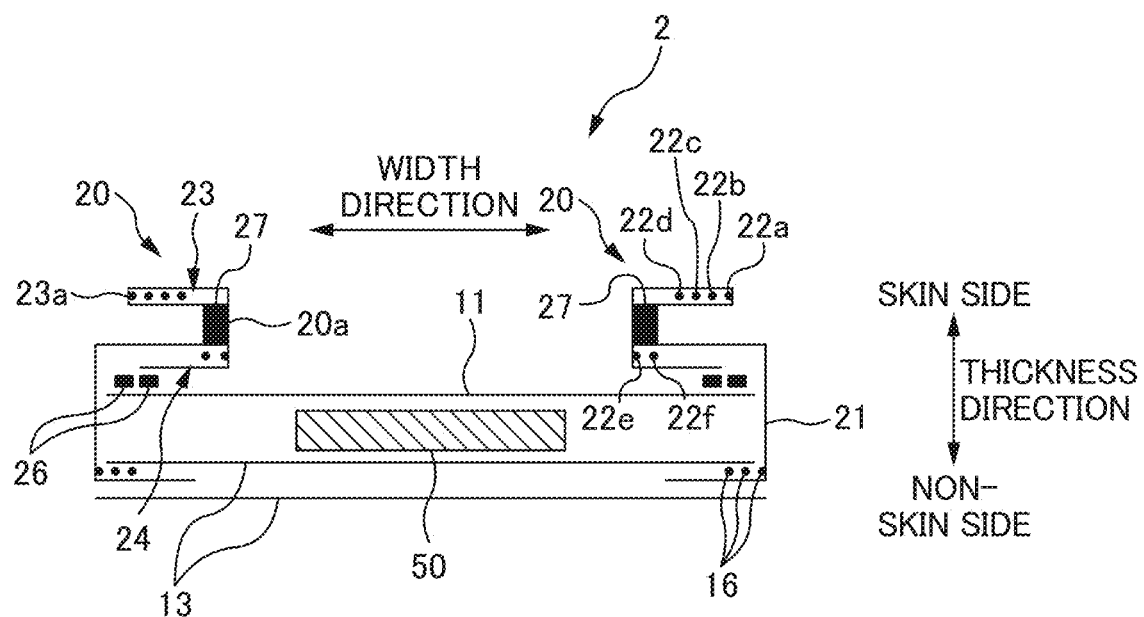
FIG. 10 is a I-I line sectional view of FIG. 9.
Figure 11A:
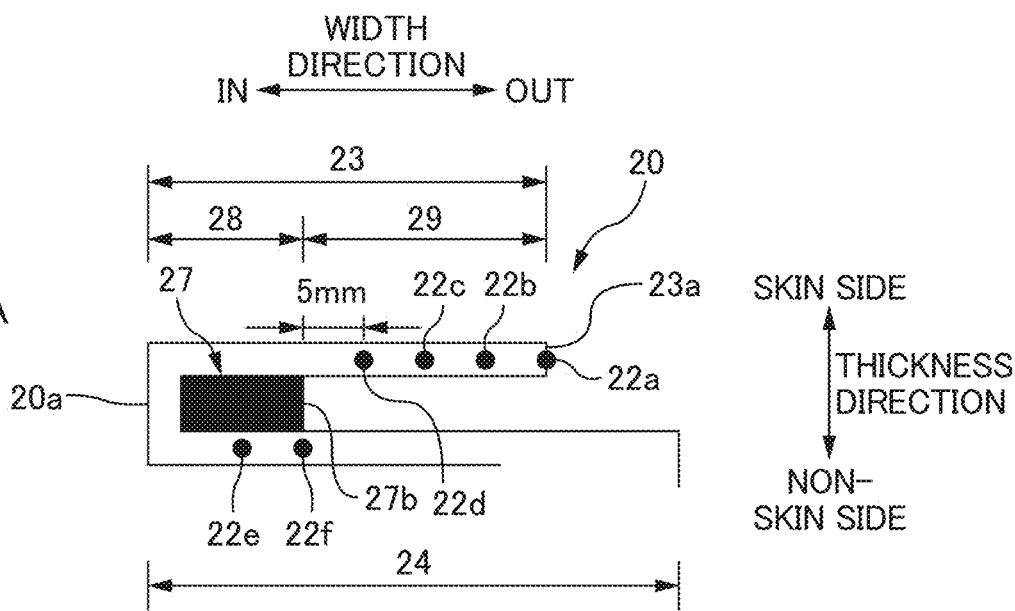
FIG. 11A and FIG. 11B are explanatory diagrams of disposition of leak-proof-wall elastic members 22a to 22f and a pinching-joined part 27 and FIG. 11C is a schematic sectional view showing standing of a leak-proof wall 20 in FIG. 11A.
Figure 11B:
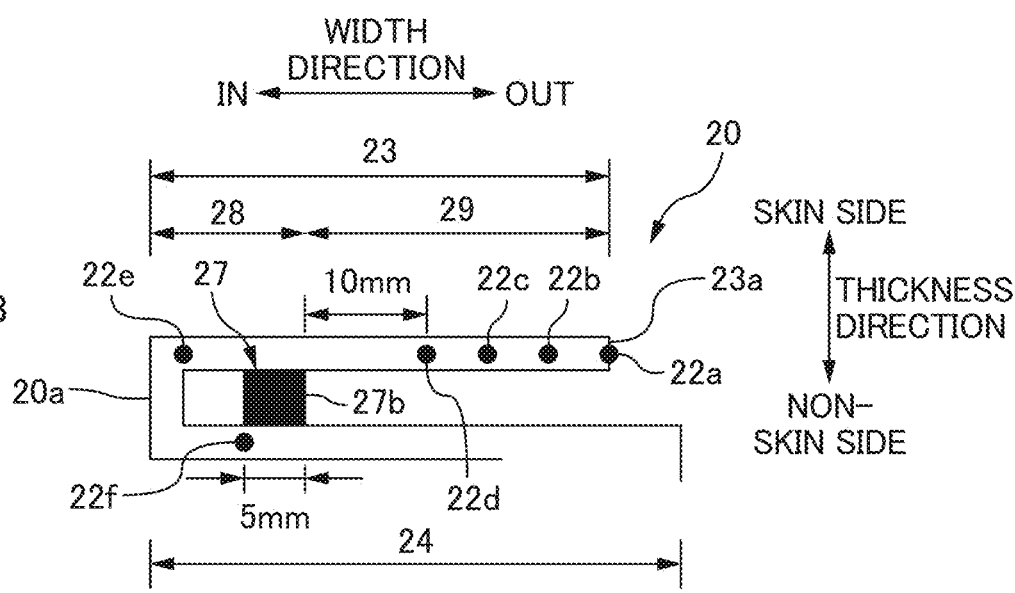
Figure 11C:
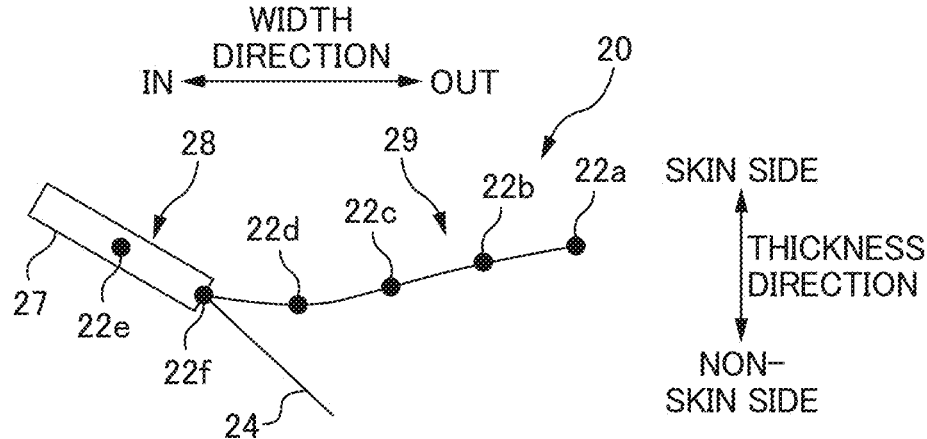

FIG. 9 is a schematic plan view of a diaper 2 in a second embodiment in an unfolded and extended state viewed from a skin side of a wearer. FIG. 10 is an I-I line sectional view of FIG. 9. FIG. 11A and FIG. 11B are explanatory diagrams of disposition of the leak-proof-wall elastic members 22a to 22f and the pinching-joined part 27. FIG. 11C is a schematic sectional view showing standing of the leak-proof wall 20 in FIG. 11A.

In the diaper 2 in the second embodiment, as in the diaper 1 in the first embodiment, the pair of leak-proof walls 20 are respectively provided on the widthwise side portions of the absorbent main body 10. The leak-proof wall 20 includes the skin-side portion 23 and the non-skin-side portion 24. The pinching-joined part 27 joins partially a surface of the skin-side portion 23 and a surface of the non-skin-side portion 24, the surfaces facing to each other. As shown in FIG. 10, the skin-side portion 23 is folded back outwardly in the width direction. The pinching-joined part 27 is provided inside the distal end 23a of the leak-proof wall 20 in the width direction.

An absorbent core 50 of the diaper 2 in the second embodiment has a rectangular shape in plan view. The absorbent core 50 does not include the pair of side low-basis-weight portions 43 and the center low-basis-weight portion 44, which are included in the absorbent core 40 (see FIG. 4) in the first embodiment.

In this case as well, the leak-proof-wall sheet 21 forming the skin-side portion 23 and the non-skin-side portion 24 is maintained folded by the pinching-joined part 27. This enables the skin-side portion 23 to come into close surface-to-surface contact with the wearer's crotch. In particular, the pinching-joined part 27 has high rigidity and therefore easily comes into close surface-to-surface contact. Accordingly, side leakage is prevented. Besides, by providing the pinching-joined part 27, the height of the leak-proof wall 20 standing is that of the non-skin-side portion 24, which is relatively low. This makes it possible to reduce a droop of the absorbent core 50.

Further, as shown in FIG. 10, it is preferable that parts 22e and 22f of the plurality of leak-proof-wall elastic members 22 of the leak-proof wall 20 are provided in a widthwise position overlapping the pinching-joined part 27. In that case, the pinching-joined part 27 can come into closer contact with the wearer's crotch with a stretching/contracting force of the leak-proof-wall elastic members 22a and 22f.

Note that, in FIG. 10, the pinching-joined part 27 is provided at an inner widthwise side end 20a of the leak-proof wall 20. However, the present invention is not limited thereto. As shown in FIG. 11B, the pinching-joined part 27 may be provided outwardly apart from the inner side end 20a of the leak-proof wall 20. In that case, it is preferable that the leak-proof-wall elastic members 22e and 22f are each provided at at least either one of a widthwise position where the elastic member overlaps the pinching-joined part 27 and a widthwise position inside the pinching-joined part 27. In this case as well, the pinching-joined part 27 can come into closer contact with the wearer's crotch with a stretching/contracting force of the leak-proof-wall elastic members 22a and 22f.

In the diaper 1 (see FIG. 5) in the first embodiment, the pinching-joined part 27 is provided in the longitudinal central portion of the absorbent main body 10 and is not provided at the longitudinal end portions. However, the present invention is not limited thereto. As in the diaper 2 of the second embodiment, the pinching-joined part 27 may be provided over the entire longitudinal region of the absorbent main body 10. In that case, the skin-side portion 23 (in particular, the pinching-joined part 27) can come into close surface-to-surface contact with the wearer over the entire longitudinal region of the leak-proof wall 20.

In the diaper 1 in the first embodiment (see FIG. 5), the maximum width of the absorbent main body 10 and the maximum width of the absorbent core 40 coincide with each other. The leak-proof wall 20 is disposed placed on the absorbent core 40 in the thickness direction. The width of the absorbent core in the first embodiment is different depending on a longitudinal position. Accordingly, depending on a longitudinal position, the leak-proof wall 20 overlaps or does not overlap the absorbent core 40.

On the other hand, in the diaper 2 in the second embodiment, the maximum width of the absorbent main body 10 is larger than the maximum width of the absorbent core 50. The width of the absorbent core 50 is uniform. Accordingly, as shown in FIG. 9, in the unfolded and extended state of the diaper 2, the skin-side portion 23, the non-skin-side portion 24, and the pinching-joined part 27 included in the leak-proof wall 20 are disposed outside the absorbent core 50 in the width direction.

Accordingly, the skin-side portion 23, the non-skin-side portion 24, and the pinching-joined part 27 do not overlap the absorbent core 50 over the entire longitudinal region. The factor for the leak-proof wall 20 to stand is uniform. This makes it uniform the standing height of the skin-side portion 23, the non-skin-side portion 24, and the pinching-joined part irrespective of the longitudinal position, making it possible to come into close contact with the wearer.

The end joined parts 25 provided at the longitudinal end portions of the leak-proof wall 20 do not overlap the absorbent core 50 either. That is, placed are at the same height the base point (the end joined part 25) of the leak-proof wall 20 standing and a standing portion (the skin-side portion 23, etc.) of the leak-proof wall 20. Accordingly, the skin-side portion 23, the non-skin-side portion 24, and the pinching-joined part 27 can securely stand.

As shown in FIG. 11A and the like, the leak-proof wall 20 includes, in the width direction, an inner gather section 28 and an outer gather section 29; The inner gather section 28 is a region from the inner side end 20a of the leak-proof wall 20 to an outer side end 27b of the pinching-joined part 27, and the outer gather section 29 is a region from the outer side end 27b of the pinching-joined part 27 to the distal end 23a (the outer side end of the skin-side portion 23) of the leak-proof wall 20.

The inner gather section 28 stands to the skin side in the thickness direction according to contraction of the inner leak-proof-wall elastic members 22e and 22f (inner elastic members) each of which is provided at at least either one of the widthwise position where the elastic member overlaps the pinching-joined part 27 and the widthwise position inside the pinching-joined part 27. The outer gather section 29 stands to, in the width direction, the skin side in the thickness direction according to contraction of the outer leak-proof-wall elastic members 22a and 22d (outer elastic members) provided in the position outside the pinching-joined part 27. The pinching-joined part 27 has high rigidity and easily becomes a base point of the bending. Accordingly, the inner gather section 28 and the outer gather section 29 stand on a base point, which is the outer widthwise side end 27b of the pinching-joined part 27.

However, if the outer gather section 29 stands excessively with respect to the inner gather section 28, the inner gather section 28 and the outer gather section 29 form a V shape, or the outer gather section 29 curls to the inner side in the width direction. Then, the outer gather section 29 cannot come into close surface-to-surface contact with the wearer's crotch.

Accordingly, as shown in FIG. 11A and FIG. 11B, it is preferable that the minimum widthwise length from the outer side end 27b of the pinching-joined part 27 to the outer leak-proof-wall elastic members 22a to 22d is larger than the minimum widthwise length from the outer side end 27b of the pinching-joined part 27 to the inner leak-proof-wall elastic members 22e and 22f.

Specifically, in FIG. 11A, the length from the outer side end 27b of the pinching-joined part 27 to the inner leak-proof-wall elastic member 22f closest to the outer side end 27b is 0 mm. On the other hand, the length from the outer side end 27b of the pinching-joined part 27 to the outer leak-proof-wall elastic member 22d closest to the outer side end 27b is 5 mm.

In FIG. 11B, the length from the outer side end 27b of the pinching-joined part 27 to the inner leak-proof-wall elastic member 22f closest to the outer side end 27b is 5 mm. On the other hand, the length from the outer side end 27b of the pinching-joined part 27 to the outer leak-proof-wall elastic member 22d closest to the outer side end 27b is 10 mm.

The leak-proof wall 20 more easily stands as the leak-proof-wall elastic member 22 is disposed closer to the outer side end 27b of the pinching-joined part 27 that becomes a base point of the standing. Accordingly, by disposing the leak-proof-wall elastic members 22a to 22f as explained above, it is possible to prevent the outer gather section 29 from standing excessively with respect to the inner gather section 28. Accordingly, as shown in FIG. 11C, the outer gather section 29 easily maintains a surface shape, that is, easily maintains a state in which the outer gather section 29 spreads in the width direction. The outer gather section 29 can be brought into close surface-to-surface contact with the crotch part of the wearer.

The outer gather section 29 may have a smaller longitudinal stretching/contracting force per unit width in the width direction than that of the inner gather section 28 has. To reduce the longitudinal stretching/contracting force per unit width, it is desirable to reduce the diameter of the leak-proof-wall elastic member 22, reduce rate of stretch of the leak-proof-wall elastic member 22, reduce an effective length of the leak-proof-wall elastic member 22, or reduce the number of the leak-proof-wall elastic members 22 per unit width.

In this case as well, it is possible to prevent the outer gather section 29 from standing excessively with respect to the inner gather section 28. Accordingly, as shown in FIG. 11C, the outer gather section 29 easily maintains a surface shape. The outer gather section 29 can be brought into close surface-to-surface contact with the crotch part of the wearer.

Note that comparison of the stretching/contracting forces of the inner gather section 28 and the outer gather section 29 is performed in the same method as comparison of the stretching/contracting forces of the inner side portion 20A and the outer widthwise side portion 20B of the leak-proof wall 20 explained in the first embodiment. To explain simply, the comparison can be performed as follow: cutting out respectively the inner gather section 28 and the outer gather section 29 including the entire range of the effective length of the leak-proof-wall elastic member 22, preparing samples; and comparing loads measured by a tensile test machine.

A disposition relation between the outer side end 27b of the pinching-joined part 27 and the leak-proof-wall elastic members 22a to 22f and a relation between the stretching/contracting forces of the inner gather section 28 and the outer gather section 29 shown in FIG. 11A and FIG. 11B may be adopted in the diaper 1 in the first embodiment. The same effect is obtained in that case.

In the diaper 1 in the first embodiment, the exterior body includes the crotch portion. However, as in the diaper 2 in the second embodiment, the configuration may be employed in which the exterior body includes only the front waist portion 51 and the back waist portion 52.

The embodiment of the present invention is explained above. However, the embodiment is for facilitating understanding of the present invention and is not for limitedly interpreting the present invention. The present invention can be changed or improved without departing from the spirit of the present invention. It goes without saying that equivalents of the present invention are included in the present invention.

For example, the present invention may be applied to absorbent articles such as a pull-on disposable diaper for children, a tape-type diaper, and a sanitary napkin.

The invention claimed is:
1. An absorbent article comprising:
an absorbent main body including an absorbent core and having a longitudinal direction, a width direction, and a thickness direction that intersect one another,
the absorbent core including a low-basis-weight portion in a widthwise central portion,
the low-basis-weight portion being a portion in which a basis weight of the absorbent core is smaller than the basis weight in a surrounding of the portion;
a pair of leak-proof walls provided on respective widthwise side portions of the absorbent main body,
each of the leak-proof walls including an elastic member that stretches and contracts in the longitudinal direction,
each of the leak-proof walls being capable of standing on a skin side in the thickness direction,
each of the leak-proof walls including a skin-side portion and a non-skin-side portion,
the non-skin-side portion disposed on a non-skin side in the thickness direction with respect to the skin-side portion; and a joined part provided inside a distal end of each of the leak-proof walls and outside the low-basis-weight portion in the width direction,
- the joined part formed by joining at least partially a surface of the skin-side portion and a surface of the non-skin-side portion, the surfaces facing to each other,
- a part of the joined part and a part of the low-basis-weight portion at least overlapping in the longitudinal direction, wherein the absorbent core includes an upper-layer core and a lower-layer core disposed on the non-skin side in the thickness direction with respect to the upper-layer core, the low-basis-weight portion is provided in the lower-layer core, the low-basis-weight portion includes a side low-basis-weight portion provided in a widthwise side portion of the absorbent core, a part of the upper-layer core overlapping the side low-basis-weight portion in the longitudinal direction is disposed inside an outer widthwise end of the side low-basis-weight portion, a longitudinal back end portion of the joined part is located on a back side in the longitudinal direction with respect to the low-basis-weight portion, and the longitudinal back end portion is placed on the upper-layer core and the lower-layer core in the thickness direction.

2. The absorbent article according to claim 1, wherein
the joined part is disposed inside an outermost widthwise end in a part of the absorbent core, and
the part is where the low-basis-weight portion is provided.

3. The absorbent article according to claim 1, wherein
a widthwise length of the low-basis-weight portion is larger than a widthwise length of the joined part.

4. The absorbent article according to claim 1, wherein
a widthwise length of the non-skin-side portion is larger than a widthwise length of the skin-side portion.

5. The absorbent article according to claim 1, wherein
a longitudinal length of the joined part is larger than a longitudinal length of the low-basis-weight portion.

6. The absorbent article according to any one of claim 1, wherein
a longitudinal center of the low-basis-weight portion and a longitudinal center of the joined part are located on a front side with respect to a longitudinal center of the absorbent article.

7. An absorbent article, comprising:
an absorbent main body including an absorbent core and having a longitudinal direction, a width direction, and a thickness direction that intersect one another,
- the absorbent core including a low-basis-weight portion in a widthwise central portion,
- the low-basis-weight portion being a portion in which a basis weight of the absorbent core is smaller than the basis weight in a surrounding of the portion;

a pair of leak-proof walls provided on respective widthwise side portions of the absorbent main body,
- each of the leak-proof walls including an elastic member that stretches and contracts in the longitudinal direction,
- each of the leak-proof walls being capable of standing on a skin side in the thickness direction,
- each of the leak-proof walls including a skin-side portion and a non-skin-side portion,
- the non-skin-side portion disposed on a non-skin side in the thickness direction with respect to the skin-side portion; and a joined part provided inside a distal end of each of the leak-proof walls and outside the low-basis-weight portion in the width direction,
- the joined part formed by joining at least partially a surface of the skin-side portion and a surface of the non-skin-side portion, the surfaces facing to each other,
- a part of the joined part and a part of the low-basis-weight portion at least overlapping in the longitudinal direction, wherein an inner widthwise side portion of the skin-side portion and the non-skin-side portion includes a plurality of the elastic members, an outer widthwise side portion of the skin-side portion includes a plurality of the elastic members, and a longitudinal stretching/contracting force per unit width in the width direction of the inner widthwise side portion is equal to or larger than a longitudinal stretching/contracting force per unit width in the width direction of the outer widthwise side portion.

8. The absorbent article according to claim 1, wherein
the absorbent article further comprises an exterior body including
- a front waist portion located on one end side of the absorbent main body,
- a back waist portion located on another end side of the absorbent main body, and
- a crotch portion located between the front waist portion and the back waist portion, the joined part is at least disposed in a position where a part of the crotch portion overlaps in the longitudinal direction, the absorbent article is of a pull-on disposable type in which widthwise side portions of the back waist portion are joined to respective widthwise side portions of the front waist portion, the absorbent article has an up-down direction and the width direction, and in an appearance of the absorbent article from a front waist portion side, at least a part of one of the leak-proof walls in a lower end region in the up-down direction is exposed from the exterior body in the width direction.

9. An absorbent article comprising:
an absorbent main body including an absorbent core and having a longitudinal direction, a width direction, and a thickness direction that intersect one another;

a pair of leak-proof walls provided on respective widthwise side portions of the absorbent main body,
- each of the leak-proof walls including an elastic member that stretches and contracts in the longitudinal direction,
- each of the leak-proof walls being capable of standing on a skin side in the thickness direction,
- each of the leak-proof walls including a skin-side portion and a non-skin-side portion,
- the non-skin-side portion disposed on a non-skin side in the thickness direction with respect to the skin-side portion; and a joined part provided inside a distal end of each of the leak-proof walls in the width direction, the joined part formed by joining at least partially a surface of the skin-side portion and a surface of the non-skin-side portion, the surfaces facing to each other, wherein
the elastic member is provided at at least either one of a widthwise position inside the joined part and a widthwise position where the elastic member overlaps the joined part,
the elastic member includes, in the width direction:
  an inner elastic member provided in at least either one of and a position inside the joined part and a position where the elastic member overlaps the joined part; and
  an outer elastic member provided in a position outside the joined part, and
a minimum widthwise length from an outer side end of the joined part to the outer elastic member is larger than a minimum widthwise length from the outer side end of the joined part to the inner elastic member.

10. An absorbent article comprising:
an absorbent main body including an absorbent core and having a longitudinal direction, a width direction, and a thickness direction that intersect one another;
a pair of leak-proof walls provided on respective widthwise side portions of the absorbent main body,
  each of the leak-proof walls including an elastic member that stretches and contracts in the longitudinal direction,
  each of the leak-proof walls being capable of standing on a skin side in the thickness direction,
  each of the leak-proof walls including a skin-side portion and a non-skin-side portion,
  the non-skin-side portion disposed on a non-skin side in the thickness direction with respect to the skin-side portion; and
a joined part provided inside a distal end of each of the leak-proof walls in the width direction, the joined part formed by joining at least partially a surface of the skin-side portion and a surface of the non-skin-side portion, the surfaces facing to each other,
wherein
the skin-side portion, the non-skin-side portion, and the joined part are disposed outside the absorbent core in the width direction,
the elastic member includes, in the width direction:
  an inner elastic member provided in at least either one of and a position inside the joined part and a position where the elastic member overlaps the joined part; and
  an outer elastic member provided in a position outside the joined part, and
a minimum widthwise length from an outer side end of the joined part to the outer elastic member is larger than a minimum widthwise length from the outer side end of the joined part to the inner elastic member.

11. An absorbent article, comprising:
an absorbent main body including an absorbent core and having a longitudinal direction, a width direction, and a thickness direction that intersect one another;
a pair of leak-proof walls provided on respective widthwise side portions of the absorbent main body,
  each of the leak-proof walls including an elastic member that stretches and contracts in the longitudinal direction,
  each of the leak-proof walls being capable of standing on a skin side in the thickness direction,
  each of the leak-proof walls including a skin-side portion and a non-skin-side portion,
  the non-skin-side portion disposed on a non-skin side in the thickness direction with respect to the skin-side portion; and
a joined part provided inside a distal end of each of the leak-proof walls in the width direction, the joined part formed by joining at least partially a surface of the skin-side portion and a surface of the non-skin-side portion, the surfaces facing to each other,
wherein
the elastic member is provided at at least either one of a widthwise position inside the joined part and a widthwise position where the elastic member overlaps the joined part,
the elastic member includes, in the width direction:
  an inner elastic member provided in at least either one of and a position inside the joined part and a position where the elastic member overlaps the joined part; and
  an outer elastic member provided in a position outside the joined part,
each of the leak-proof walls includes, in the width direction:
  an inner gather section from an inner side end of the leak-proof wall to an outer side end of the joined part; and
  an outer gather section from the outer side end of the joined part to the distal end of the leak-proof wall, and
the outer gather section has a smaller longitudinal stretching/contracting force per unit width in the width direction than that of the inner gather section.

12. An absorbent article comprising:
an absorbent main body including an absorbent core and having a longitudinal direction, a width direction, and a thickness direction that intersect one another;
a pair of leak-proof walls provided on respective widthwise side portions of the absorbent main body,
  each of the leak-proof walls including an elastic member that stretches and contracts in the longitudinal direction,
  each of the leak-proof walls being capable of standing on a skin side in the thickness direction,
  each of the leak-proof walls including a skin-side portion and a non-skin-side portion,
  the non-skin-side portion disposed on a non-skin side in the thickness direction with respect to the skin-side portion; and
a joined part provided inside a distal end of each of the leak-proof walls in the width direction, the joined part formed by joining at least partially a surface of the skin-side portion and a surface of the non-skin-side portion, the surfaces facing to each other,
wherein
the skin-side portion, the non-skin-side portion, and the joined part are disposed outside the absorbent core in the width direction,
the elastic member includes, in the width direction:
  an inner elastic member provided in at least either one of and a position inside the joined part and a position where the elastic member overlaps the joined part; and
  an outer elastic member provided in a position outside the joined part,
each of the leak-proof walls includes, in the width direction:

an inner gather section from an inner side end of the leak-proof wall to an outer side end of the joined part; and an outer gather section from the outer side end of the joined part to the distal end of the leak-proof wall, and the outer gather section has a smaller longitudinal stretching/contracting force per unit width in the width direction than that of the inner gather section.

\* \* \* \* \*